(12) United States Patent
Jennewein et al.

(10) Patent No.: US 11,898,185 B2
(45) Date of Patent: Feb. 13, 2024

(54) PROCESS FOR THE PRODUCTION OF FUCOSYLATED OLIGOSACCHARIDES

(71) Applicant: Chr. Hansen HMO GmbH, Rheinbreitbach (DE)

(72) Inventors: Stefan Jennewein, Bad Honnef (DE); Dirk Wartenberg, Bonn (DE); Katja Parschat, Bonn (DE)

(73) Assignee: Chr Hansen HMO GmbH, Rheinbreitbach (DE)

( * ) Notice: Subject to any disclaimer, the term of this patent is extended or adjusted under 35 U.S.C. 154(b) by 0 days.

(21) Appl. No.: 16/345,535

(22) PCT Filed: Oct. 24, 2017

(86) PCT No.: PCT/EP2017/077192
§ 371 (c)(1),
(2) Date: Apr. 26, 2019

(87) PCT Pub. No.: WO2018/077892
PCT Pub. Date: May 3, 2018

(65) Prior Publication Data
US 2019/0309336 A1 Oct. 10, 2019

(30) Foreign Application Priority Data
Oct. 29, 2016 (EP) .................... 16196486

(51) Int. Cl.
| | | |
|---|---|---|
| *C12P 19/18* | (2006.01) | |
| *C12N 9/04* | (2006.01) | |
| *C12N 9/10* | (2006.01) | |
| *C12N 9/12* | (2006.01) | |
| *C12N 9/16* | (2006.01) | |
| *C12N 9/88* | (2006.01) | |
| *C12N 9/90* | (2006.01) | |
| *C12N 15/52* | (2006.01) | |
| *C12N 15/70* | (2006.01) | |
| *C07K 14/24* | (2006.01) | |

(52) U.S. Cl.
CPC .............. *C12P 19/18* (2013.01); *C07K 14/24* (2013.01); *C12N 9/0006* (2013.01); *C12N 9/1051* (2013.01); *C12N 9/12* (2013.01); *C12N 9/1205* (2013.01); *C12N 9/1241* (2013.01); *C12N 9/16* (2013.01); *C12N 9/88* (2013.01); *C12N 9/90* (2013.01); *C12N 15/52* (2013.01); *C12N 15/70* (2013.01); *C12Y 101/01271* (2013.01); *C12Y 204/01065* (2013.01); *C12Y 207/01011* (2013.01); *C12Y 207/07013* (2013.01); *C12Y 401/02013* (2013.01); *C12Y 402/01047* (2013.01); *C12Y 504/02008* (2013.01)

(58) Field of Classification Search
CPC .... C12P 1/04; C12P 19/04; C12P 9/18; C12Y 204/01069; C12Y 204/01065
See application file for complete search history.

(56) References Cited

U.S. PATENT DOCUMENTS

| | | | |
|---|---|---|---|
| 9,453,230 B2 | 9/2016 | Merighi et al. | |
| 10,738,336 B2 | 8/2020 | Beauprez et al. | |
| 2002/0025560 A1 | 2/2002 | Koizumi et al. | |
| 2009/0082307 A1* | 3/2009 | Samain ................... | A61P 29/00 514/54 |
| 2009/0104655 A1 | 4/2009 | Buchs et al. | |
| 2011/0300584 A1 | 12/2011 | Huefner et al. | |
| 2013/0122553 A1* | 5/2013 | Maertens ........ | C12Y 302/01026 435/97 |
| 2014/0024820 A1* | 1/2014 | Parkot ................... | C12P 21/005 536/23.2 |
| 2014/0349348 A1* | 11/2014 | Beauprez ............. | C07K 14/245 435/100 |
| 2015/0240277 A1* | 8/2015 | Jennewein ........... | C12N 9/1051 435/97 |
| 2016/0153012 A1* | 6/2016 | Marliere .................. | C12N 9/88 435/119 |
| 2016/0186223 A1* | 6/2016 | Jennewein .............. | C12P 19/12 435/100 |
| 2017/0175154 A1* | 6/2017 | Samain ................ | C07K 14/245 |
| 2017/0298363 A1* | 10/2017 | Pharkya .................... | C12P 7/18 |

FOREIGN PATENT DOCUMENTS

| | | |
|---|---|---|
| EP | 2479263 A1 | 7/2012 |
| EP | 3315610 B1 | 12/2020 |
| JP | 2012529274 A | 11/2012 |
| JP | 2015504654 A | 2/2015 |
| KR | 101544184 B1 | 8/2015 |
| WO | 2010/070104 A1 | 6/2010 |

(Continued)

OTHER PUBLICATIONS

MetaCYC (2022, updated) https://biocyc.org/META/NEW IMAGE? object=F16BDEPHOS-RXN, pp. 1-2.*

(Continued)

*Primary Examiner* — Anand U Desai
(74) *Attorney, Agent, or Firm* — McNeill Baur PLLC

(57) ABSTRACT

The present invention relates to a method for producing fucosylated oligosaccharides by using a recombinant prokaryotic host cell that is cultivated on a gluconeogenic substrate, as well as to the host cell and its use. The host cell is genetically modified in that the activity of a fructose-6-phosphate converting enzyme is abolished or lowered, and the transport of the produced fucosylated oligosaccharide through the cell membrane is facilitated by an exogenous transport protein.

18 Claims, 14 Drawing Sheets

Specification includes a Sequence Listing.

(56) References Cited

FOREIGN PATENT DOCUMENTS

| WO | 2010142305 | A1 | 12/2010 |
|---|---|---|---|
| WO | 2012007481 | A2 | 1/2012 |
| WO | 2012049083 | A2 | 4/2012 |
| WO | 2013087884 | A1 | 6/2013 |
| WO | 2014018596 | A2 | 1/2014 |
| WO | 2015150328 | A1 | 10/2015 |
| WO | 2015197082 | A1 | 12/2015 |
| WO | 2016040531 | A1 | 3/2016 |
| WO | 2016075243 | A1 | 5/2016 |
| WO | 2016/153300 | A1 | 9/2016 |

OTHER PUBLICATIONS

Third Party Observation for European application No. 20160196486 dated May 14, 2019.
Chin et al., "Metabolic engineering of Escherichia coli to produce 2'-fucosyllactose via salvage pathway of guanosine 5'-diphosphate (GDP)-L-fucose", Biotechnology and Bioengineering, Jun. 20, 2016, pp. 2443-2452, vol. 113.
Chin et al., "Metabolic engineering of Corynebacterium glutamicum to produce GDP-L-fucose from glucose and mannose", Bioprocess and Biosystems Engineering, 2013, pp. 749-756, vol. 36.
Chin et al., "Enhanced production of 2'-fucosyllactose in engineered Escherichia coli BL21star(DE3) by modulation of lactose metabolism and fucosyltransferase", Journal of Biotechnology, 2015, pp. 107-115, vol. 210.
Petschacher et al., "Biotechnological production of fucosylated human milk oligosaccharides: prokaryotic fucosyltransferases and their use in biocatalytic cascades or whole cell conversion systems", Journal of Biotechnology, Apr. 1, 2016, pp. 61-83, vol. 235.
Engels et al., "WbgL: a novel bacterial alpha-1,2-fucosyltransferase for the synthesis of 2'-fucosyllactose", Glycobiology, 2014, pp. 170-178, vol. 24.
Baumgartner et al., "Construction of Escherichia coli strains with chromosomally integrated expression cassettes for the synthesis of 2'-fucosyllactose", Microbial Cell Factories, 2013, pp. 1-13, vol. 12.
Huang et al., "Metabolic engineering of Escherichia coli for the production of 2'-fucosyllactose and 3-fucosyllactose through modular pathway enhancement", Metabolic Engineering, Mar. 9, 2017, pp. 23-38, vol. 41.
Weichert et al., "Bioengineered 2'-fucosyllactose and 3-fucosyllactose inhibit the adhesion of Pseudomonas aeruginosa and enteric pathogens to human intestinal and respiratory cell lines", Nutrition Research, 2013, pp. 831-833, vol. 33.
International Search Report and Written Opinion of International Patent Application No. PCT/EP2017/077192 dated Feb. 9, 2018.
Alignment of Pisum sativum FBPases, Sep. 2, 2021, 2 pages.
Appendix K, Description and Safety Evaluation of E. coli BL21 #1540, from GRN 571 (GRAS Notice), 20 pages.
Drouillard et al., "Large-Scale Synthesis of H-Antigen Oligosaccharides by Expressing Helicobacter pylori [alpha] 1,2-Fucosyltransferase in Metabolically Engineered Escherichia coli Cells.", Angew. Chem. Int. Ed., Feb. 2006, pp. 1778-1780, vol. 45.
FDA, GRAS Notices, GRN No. 571, Nov. 6, 2015, 1 page.
Fraenkel, Glycolysis, Section A1, Central Metabolism, E.coli and Salmonella typhinmurium, ASM Press, 1996, 4 pages.
Gottlieb et al., "Improvement of L-phenylalanine production from glycerol by recombinant Escherichia coli strains: The role of extra copies of glpK, glpX, and tktA genes," Microbial Cell Factories, 2014, 13:96, 16 pages.
Jacquot et al., "Cysteine-153 is required for redox regulation of pea chloroplast fructose-1,6-bisphosphatase," FEBS Letters, 1997, 401:143-147.
Lee et al., "Whole cell biosynthesis of a functional oligosaccharide, 2'-fucosyllactose, using engineered Escherichia coli," Microbial Cell Factories, 2012, 11(48): 1-9.
Lin, Dissimilatory Pathways for Sugars, Polyols, and Carboxylates, Section A3, E.coli and Salmonella typhimurium, 1996, ASM Press, 11 pages.
Machine translation of KR101544184, dated Aug. 21, 2015, Seo et al, Abstract only, 1 page.

* cited by examiner

Fig. 3

SEQ ID No. 1

P_tet-manCB,P_T5-gmd-wcaG-FRT-dhfr-FRT

GCCAGATGATTAATTCCTAATTTTTGTTGACACTCTATCATTGATAGAGTTATTTTACCA
CTCCCTATCAGTGATAGAGAAAAGTGAAATGAATAGTTCGACAAAAATCTAGAAATAATT
TTGTTTAACTTTAAGAAGGAGATATACAATTTCGTCGACACACAGGAAACATATTAAAAA
TTAAAACCTGCAGGAGTTTGAAGGAGATAGAACCATGGCGCAGTCGAAACTCTATCCAGT
TGTGATGGCAGGTGGCTCCGGTAGCCGCTTATGGCCGCTTTCCCGCGTACTTTATCCCAA
GCAGTTTTTATGCCTGAAAGGCGATCTCACCATGCTGCAAACCACCATCTGCCGCCTGAA
CGGCGTGGAGTGCGAAAGCCCGGTGGTGATTTGCAATGAGCAGCACCGCTTTATTGTCGC
GGAACAGCTGCGTCAACTGAACAAACTTACCGAGAACATTATTCTCGAACCGGCAGGGCG
AAACACGGCACCTGCCATTGCGCTGGCGGCGCTGGCGGCAAAACGTCATAGCCCGGAGAG
CGACCCGTTAATGCTGGTATTGGCGGCGGATCATGTGATTGCCGATGAAGACGCGTTCCG
TGCCGCCGTGCGTAATGCCATGCCATATGCCGAAGCGGGCAAGCTGGTGACCTTCGGCAT
TGTGCCGGATCTACCAGAAACCGGTTATGGCTATATTCGTCGCGGTGAAGTGTCTGCGGG
TGAGCAGGATATGGTGGCCTTTGAAGTGGCGCAGTTTGTCGAAAAACCGAATCTGGAAAC
CGCTCAGGCCTATGTGGCAAGCGGCGAATATTACTGGAACAGCGGTATGTTCCTGTTCCG
CGCCGGACGCTATCTCGAAGAACTGAAAAAATATCGCCCGGATATCCTCGATGCCTGTGA
AAAAGCGATGAGCGCCGTCGATCCGGATCTCAATTTTATTCGCGTGGATGAAGAAGCGTT
TCTCGCCTGCCCGGAAGAGTCGGTGGATTACGCGGTCATGGAACGTACGGCAGATGCTGT
TGTGGTGCCGATGGATGCGGGCTGGAGCGATGTTGGCTCCTGGTCTTCATTATGGGAGAT
CAGCGCCCACACCGCCGAGGGCAACGTTTGCCACGGCGATGTGATTAATCACAAAACTGA
AAACAGCTATGTGTATGCTGAATCTGGCCTGGTCACCACCGTCGGGGTGAAAGATCTGGT
AGTGGTGCAGACCAAAGATGCGGTGCTGATTGCCGACCGTAACGCGGTACAGGATGTGAA
AAAAGTGGTCGAGCAGATCAAAGCCGATGGTCGCCATGAGCATCGGGTGCATCGCGAAGT
GTATCGTCCGTGGGGCAAATATGACTCTATCGACGCGGGCGACCGCTACCAGGTGAAACG
CATCACCGTGAAACCGGGCGAGGGCTTGTCGGTACAGATGCACCATCACCGCGCGGAACA
CTGGGTGGTTGTCGCGGGAACGGCAAAAGTCACCATTGATGGTGATATCAAACTGCTTGG
TGAAAACGAGTCCATTTATATTCCGCTGGGGGCGACGCATTGCCTGGAAAACCCGGGGAA
AATTCCGCTCGATTTAATTGAAGTGCGCTCCGGCTCTTATCTCGAAGAGGATGATGTGGT
GCGTTTCGCGGATCGCTACGGACGGGTGTAAACGTCGCATCAGGCAATGAATGCGAAACC
GCGGTGTAAATAACGACAAAAATAAAATTGGCCGCTTCGGTCAGGGCCAACTATTGCCTG
AAAAAGGGTAACGATATGAAAAAATTAACCTGCTTTAAAGCCTATGATATTCGCGGGAAA
TTAGGCGAAGAACTGAATGAAGATATCGCCTGGCGCATTGGTCGCGCCTATGGCGAATTT
CTCAAACCGAAAACCATTGTGTTAGGCGGTGATGTCCGCCTCACCAGCGAAACCTTAAAA
CTGGCGCTGGCGAAAGGTTTACAGGATGCGGGCGTTGACGTGCTGGATATTGGTATGTCC
GGCACCGAAGAGATCTATTTCGCCACGTTCCATCTCGGCGTGGATGGCGGCATTGAAGTT
ACCGCCAGCCATAATCCGATGGATTATAACGGCATGAAGCTGGTTCGCGAGGGGGCTCGC

```
CCGATCAGCGGAGATACCGGACTGCGCGACGTCCAGCGTCTGGCTGAAGCCAACGACTTT
CCTCCCGTCGATGAAACCAAACGCGGTCGCTATCAGCAAATCAACCTGCGTGACGCTTAC
GTTGATCACCTGTTCGGTTATATCAATGTCAAAAACCTCACGCCGCTCAAGCTGGTGATC
AACTCCGGGAACGGCGCAGCGGGTCCGGTGGTGGACGCCATTGAAGCCCGCTTTAAAGCC
CTCGGCGCGCCCGTGGAATTAATCAAAGTGCACAACACGCCGGACGGCAATTTCCCCAAC
GGTATTCCTAACCCACTACTGCCGGAATGCCGCGACGACACCCGCAATGCGGTCATCAAA
CACGGCGCGGATATGGGCATTGCTTTTGATGGCGATTTTGACCGCTGTTTCCTGTTTGAC
GAAAAGGGCAGTTTATTGAGGGCTACTACATTGTCGGCCTGTTGGCAGAAGCATTCCTC
GAAAAAAATCCCGGCGCGAAGATCATCCACGATCCACGTCTCTCCTGGAACACCGTTGAT
GTGGTGACTGCCGCAGGTGGCACGCCGGTAATGTCGAAAACCGGACACGCCTTTATTAAA
GAACGTATGCGCAAGGAAGACGCCATCTATGGTGGCGAAATGAGCGCCCACCATTACTTC
CGTGATTTCGCTTACTGCGACAGCGGCATGATCCCGTGGCTGCTGGTCGCCGAACTGGTG
TGCCTGAAAGATAAAACGCTGGGCGAACTGGTACGCGACCGGATGGCGGCGTTTCCGGCA
AGCGGTGAGATCAACAGCAAACTGGCGCAACCCGTTGAGGCGATTAACCGCGTGGAACAG
CATTTTAGCCGTGAGGCGCTGGCGGTGGATCGCACCGATGGCATCAGCATGACCTTTGCC
GACTGGCGCTTTAACCTGCGCACCTCCAATACCGAACCGGTGGTGCGCCTGAATGTGGAA
TCGCGCGGTGATGTGCCGCTGATGGAAGCGCGAACGCGAACTCTGCTGACGTTGCTGAAC
GAGTAAAACGCGGCCGCGATATCGTTGTAAAACGACGGCCAGTGCAAGAATCATAAAAA
ATTTATTTGCTTTCAGGAAAATTTTTCTGTATAATAGATTCATAAATTTGAGAGAGGAGT
TTTTGTGAGCGGATAACAATTCCCCATCTTAGTATATTAGTTAAGTATAAATACACCGCG
GAGGACGAAGGAGATAGAACCATGTCAAAGTCGCTCTCATCACCGGTGTAACCGGACAA
GACGGTTCTTACCTGGCAGAGTTTCTGCTGGAAAAAGGTTACGAGGTGCATGGTATTAAG
CGTCGCGCATCGTCATTCAACACCGAGCGCGTGGATCACATTTATCAGGATCCGCACACC
TGCAACCCGAAATTCCATCTGCATTATGGCGACCTGAGTGATACCTCTAACCTGACGCGC
ATTTTGCGTGAAGTACAGCCGGATGAAGTGTACAACCTGGGCGCAATGAGCCACGTTGCG
GTCTCTTTTGAGTCACCAGAATATACCGCTGACGTCGACGCGATGGGTACGCTGCGCCTG
CTGGAGGCGATCCGCTTCCTCGGTCTGGAAAAGAAAACTCGTTTCTATCAGGCTTCCACC
TCTGAACTGTATGGTCTGGTGCAGGAAATTCCGCAGAAAGAGACCACGCCGTTCTACCCG
CGATCTCCGTATGCGGTCGCCAAACTGTACGCCTACTGGATCACCGTTAACTACCGTGAA
TCCTACGGCATGTACGCCTGTAACGGAATTCTCTTCAACCATGAATCCCCGCGCCGCGGC
GAAACCTTCGTTACCCGCAAAATCACCCGCGCAATCGCCAACATCGCCCAGGGGCTGGAG
TCGTGCCTGTACCTCGGCAATATGGATTCCCTGCGTGACTGGGGCCACGCCAAAGACTAC
GTAAAAATGCAGTGGATGATGCTGCAGCAGGAACAGCCGGAAGATTTCGTTATCGCGACC
GGCGTTCAGTACTCCGTGCGTCAGTTCGTGGAAATGGCGGCAGCACAGCTGGGCATCAAA
CTGCGCTTTGAAGGCACGGGCGTTGAAGAGAAGGGCATTGTGGTTTCCGTCACCGGGCAT
GACGCGCCGGGCGTTAAACCGGGTGATGTGATTATCGCTGTTGACCCGCGTTACTTCCGT
CCGGCTGAAGTTGAAACGCTGCTCGGCGACCCGACCAAAGCGCACGAAAACTGGGCTGG
AAACCGGAAATCACCCTCAGAGAGATGGTGTCTGAAATGGTGGCTAATGACCTCGAAGCG
GCGAAAAAACACTCTCTGCTGAAATCTCACGGCTACGACGTGGCGATCGCGCTGGAGTCA
TAAGCATGAGTAAACAACGAGTTTTATTGCTGGTCATCGCGGGATGGTCGGTTCCGCCA
TCAGGCGGCAGCTCGAACAGCGCGGTGATGTGGAACTGGTATTACGCACCCGCGACGAGC
TGAACCTGCTGGACAGCCGCGCCGTGCATGATTTCTTTGCCAGCGAACGTATTGACCAGG
```

Fig. 3 (cont.)

TCTATCTGGCGGCGGCGAAAGTGGGCGGCATTGTTGCCAACAACACCTATCCGGCGGATT
TCATCTACCAGAACATGATGATTGAGAGCAACATCATTCACGCCGCGCATCAGAACGACG
TGAACAAACTGCTGTTTCTCGGATCGTCCTGCATCTACCCGAAACTGGCAAAACAGCCGA
TGGCAGAAAGCGAGTTGTTGCAGGGCACGCTGGAGCCGACTAACGAGCCTTATGCTATTG
CCAAAATCGCCGGGATCAAACTGTGCGAATCATACAACCGCCAGTACGGACGCGATTACC
GCTCAGTCATGCCGACCAACCTGTACGGGCCACACGACAACTTCCACCCGAGTAATTCGC
ATGTGATCCCAGCATTGCTGCGTCGCTTCCACGAGGCGACGGCACAGAATGCGCCGGACG
TGGTGGTATGGGGCAGCGGTACACCGATGCGCGAATTTCTGCACGTCGATGATATGGCGG
CGGCGAGCATTCATGTCATGGAGCTGGCGCATGAAGTCTGGCTGGAGAACACCCAGCCGA
TGTTGTCGCACATTAACGTCGGCACGGGCGTTGACTGCACTATCCGCGAGCTGGCGCAAA
CCATCGCCAAAGTGGTGGGTTACAAAGGCCGGGTGGTTTTTGATGCCAGCAAACCGGATG
GCACGCCGCGCAAACTGCTGGATGTGACGCGCCTGCATCAGCTTGGCTGGTATCACGAAA
TCTCACTGGAAGCGGGGCTTGCCAGCACTTACCAGTGGTTCCTTGAGAATCAAGACCGCT
TTCGGGGGGGGAGCTAACGCGCCATTTAAATCAACCTCAGCGGTCATAGCTGTTTCCTGT
GACTGAGCAATAACTAGCATAACCCCTTGGGGCCTCTAAACGGGTCTTGAGGGGTTTTTT
GCTGAAACCAATTTGCCTGGCGGCAGTAGCGCGGTGGTCCCACCTGACCCCATGCCGAAC
TCAGAAGTGAAACGCCGTAGCGCCGATGGTAGTGTGGGGTCTCCCCATGCGAGAGTAGGG
AACTGCCAGGCATCAAATAAAACGAAAGGCTCAGTCGAAAGACTGGGCCTTTCGGGATCC
AGGCCGGCCTGTTAACGAATTAATCTTCCGCGGCGGTATCGATAAGCTTGATATCGAATT
CCGAAGTTCCTATTCTCTAGAAAGTATAGGAACTTCAGGTCTGAAGAGGAGTTTACGTCC
AGCCAAGCTAGCTTGGCTGCAGGTCGTCGAAATTCTACCGGGTAGGGGAGGCGCTTTTCC
CAAGGCAGTCTGGAGCATGCGCTTTAGCAGCCCCGCTGGGCACTTGGCGCTACACAAGTG
GCCTCTGGCCTCGCACACATTCCACATCCACCGGTAGGCGCCAACCGGCTCCGTTCTTTG
GTGGCCCCTTCGCGCCACCTTCTACTCCTCCCCTAGTCAGGAAGTTCCCCCCCGCCCCGC
AGCTCGCGTCGTGCAGGACGTGACAAATGGAAGTAGCACGTCTCACTAGTCTCGTGCAGA
TGGACAGCACCGCTGAGCAATGGAAGCGGGTAGGCCTTTGGGGCAGCGGCCAATAGCAGC
TTTGCTCCTTCGCTTTCTGGGCTCAGAGGCTGGGAAGGGGTGGGTCCGGGGGCGGGCTCA
GGGGCGGGCTCAGGGGCGGGGCGGGCGCCCGAAGGTCCTCCGGAGGCCCGGCATTCTGCACG
CTTCAAAAGCGCACGTCTGCCGCGCTGTTCTCCTCTTCCTCATCTCCGGGCCTTTCGA
CCTGCAGCCTGTTGACAATTAATCATCGGCATAGTATATCGGCATAGTATAATACGACAA
GGTGAGGAACTAAACCATGGGTCAAAGTAGCGATGAAGCCAACGCTCCCGTTGCAGGGCA
GTTTGCGCTTCCCCTGAGTGCCACCTTTGGCTTAGGGGATCGCGTACGCAAGAAATCTGG
TGCCGCTTGGCAGGGTCAAGTCGTCGGTTGGTATTGCACAAAACTCACTCCTGAAGGCTA
TGCGGTCGAGTCCGAATCCCACCCAGGCTCAGTGCAAATTTATCCTGTGGCTGCACTTGA
ACGTGTGGCCTAATGAGGGGATCAATTCTCTAGAGCTCGCTGATCAGAAGTTCCTATTCT
CTAGAAAGTATAGGAACTTCGATGGCGCCTCATCCCTGAAGCCAATAGGGATAACAGGGT
AAT

SEQ ID No. 2
P<sub>tag</sub>-lacY-FRT-add1-FRT
TGGCCAGATGATTAATTCCTAATTTTTGTTGACACTCTATCATTGATAGAGTTATTTTAC

Fig. 3 (cont.)

CACTCCCTATCAGTGATAGAGAAAAGTGAAATGAATAGTTCGACAAAAATCTAGAAATAA
TTTTGTTTAACTTTAAGAAGGAGATATACAAATGTACTATTTAAAAAACACAAACTTTTG
GATGTTCGGTTTATTCTTTTTCTTTTACTTTTTTATCATGGGAGCCTACTTCCCGTTTTT
CCCGATTTGGCTACATGACATCAACCATATCAGCAAAAGTGATACGGGTATTATTTTTGC
CGCTATTTCTCTGTTCTCGCTATTATTCCAACCGCTGTTTGGTCTGCTTTCTGACAAACT
CGGGCTGCGCAAATACCTGCTGTGGATTATTACCGGCATGTTAGTGATGTTTGCGCCGTT
CTTTATTTTTATCTTCGGGCCACTGTTACAATACAACATTTTAGTAGGATCGATTGTTGG
TGGTATTTATCTAGGCTTTTGTTTTAACGCCGGTGCGCCAGCAGTAGAGGCATTTATTGA
GAAAGTCAGCCGTCGCAGTAATTTCGAATTTGGTCGCGCGCGGATGTTTGGCTGTGTTGG
CTGGGCGCTGTGTGCCTCGATTGTCGGCATCATGTTCACCATCAATAATCAGTTTGTTTT
CTGGCTGGGCTCTGGCTGTGCACTCATCCTCGCCGTTTTACTCTTTTTCGCCAAAACGGA
TGCGCCCTCTTCTGCCACGGTTGCCAATGCGGTAGGTGCCAACCATTCGGCATTTAGCCT
TAAGCTGGCACTGGAACTGTTCAGACAGCCAAAACTGTGGTTTTTGTCACTGTATGTTAT
TGGCGTTTCCTGCACCTACGATGTTTTTGACCAACAGTTTGCTAATTTCTTTACTTCGTT
CTTTGCTACCGGTGAACAGGGTACGCGGGTATTTGGCTACGTAACGACAATGGGCGAATT
ACTTAACGCCTCGATTATGTTCTTTGCGCCACTGATCATTAATCGCATCGGTGGGAAAAA
CGCCCTGCTGCTGGCTGGCACTATTATGTCTGTACGTATTATTGGCTCATCGTTCGCCAC
CTCAGCGCTGGAAGTGGTTATTCTGAAAACGCTGCATATGTTTGAAGTACCGTTCCTGCT
GGTGGGCTGCTTTAAATATATTACCAGCCAGTTTGAAGTGCGTTTTTCAGCGACGATTTA
TCTGGTCTGTTTCTGCTTCTTTAAGCAACTGGCGATGATTTTTATGTCTGTACTGGCGGG
CAATATGTATGAAAGCATCGGTTCCAGGGCGCTTATCTGGTGCTGGGTCTGGTGGCGCT
GGGCTTCACCTTAATTTCCGTGTTCACGCTTAGCGGCCCCGGCCCGCTTTCCCTGCTGCG
TCGTCAGGTGAATGAAGTCGCTGGGAGCTAAGCGGCCGCGTCGACACGCAAAAAGGCCAT
CCGTCAGGATGGCCTTCTGCTTAATTTGATGCCTGGCAGTTTATGGCGGGCGTCCTGCCC
GCCACCCTCCGGGCCGTTGCTTCGCAACGTTCAAATCCGCTCCCGGCGGATTTGTCCTAC
TCAGGAGAGCGTTCACCGACAAACAACAGATAAAACGAAAGGCCCAGTCTTTCGACTGAG
CCTTTCGTTTTATTTGATGCCTGGCAGTTCCCTACTCTCGCATGGGGAGACCCCACACTA
CCATCATGTATGAATATCCTCCTTAGTTCCTATTCCGAAGTTCCTATTCTCTAGAAAGTA
TAGGAACTTCGGCGCGTCCTACCTGTGACACGCGTGCCGCAGTCTCACGCCCGGAGCGTA
GCGACCGAGTGAGCTAGCTATTTGTTTATTTTTCTAAATACATTCAAATATGTATCCGCT
CATGAGACAATAACCCTGATAAATGCTTCAATAATATTGAAAAAGGAAGAGTATGAGGGA
AGCGGTGATCGCCGAAGTATCGACTCAACTATCAGAGGTAGTTGGCGTCATCGAGCGCCA
TCTCGAACCGACGTTGCTGGCCGTACATTTGTACGGCTCCGCAGTGGATGGCGGCCTGAA
GCCACACAGTGATATTGATTTGCTGGTTACGGTGACCGTAAGGCTTGATGAAACAACGCG
GCGAGCTTTGATCAACGACCTTTTGGAAACTTCGGCTTCCCCTGGAGAGAGCGAGATTCT
CCGCGCTGTAGAAGTCACCATTGTTGTGCACGACGACATCATTCCGTGGCGTTATCCAGC
TAAGCGCGAACTGCAATTTGGAGAATGGCAGCGCAATGACATTCTTGCAGGTATCTTCGA
GCCAGCCACGATCGACATTGATCTGGCTATCTTGCTGACAAAAGCAAGAGAACATAGCGT
TGCCTTGGTAGGTCCAGCGGCGGAGGAACTCTTTGATCCGGTTCCTGAACAGGATCTATT
TGAGGCGCTAAATGAAACCTTAACGCTATGGAACTCGCCGCCCGACTGGGCTGGCGATGA
GCGAAATGTAGTGCTTACGTTGTCCCGCATTTGGTACAGCGCAGTAACCGGCAAAATCGC
GCCGAAGGATGTCGCTGCCGACTGGGCAATGGAGCGCCTGCCGGCCCAGTATCAGCCCGT

Fig. 3 (cont.)

CATACTTGAAGCTAGACAGGCTTATCTTGGACAAGAAGAAGATCGCTTGGCCTCGCGCG
AGATCAGTTGGAAGAATTTGTCCACTACGTGAAAGGCGAGATCACCAAGGTAGTCGGCAA
ATAATGTCTAACAATTCGTTCAAGCCGAGGGGCCGCAAGATCCGGCCACGATGACCCGGT
CGTCGGGTACCGGCAGGGCGGGGCGTAAGGCGCGCCATTTAAATGAAGTTCCTATTCCGA
AGTTCCTATTCTCTAGAAAGTATAGGAACTT

SEQ ID No. 3
P_tet-wbgL-FRT-neo-FRT
GGCCAGATGATTAATTCCTAATTTTTGTTGACACTCTATCATTGATAGAGTTATTTTACC
ACTCCCTATCAGTGATAGAGAAAAGTGAAATGAATAGTTCGACAAAAATCTAGAAATAAT
TTTGTTTAACTTTAAGAAGGAGATATACAAATGGGCAGCATTATTCGTCTGCAGGGTGGT
CTGGGTAATCAGCTGTTTCAGTTAGCTTTGGTTATGCCCTGAGCAAAATTAATGGTACA
CCGCTGTATTTCGACATTAGCCATTATGCCGAAAACGATGATCATGGTGGTTATCGTCTG
AATAATCTGCAGATTCCGGAAGAATATCTGCAGTATTATACCCCGAAAATTAATAATATT
TATAAACTGCTGGTGCGTGGCAGCCGTCTGTATCCGGATATTTTTCTGTTTCTGGGCTTT
TGCAACGAATTTCATGCCTATGGCTACGATTTTGAATATATTGCCCAGAAATGGAAAAGC
AAAAAATACATTGGCTACTGGCAGAGCGAACACTTTTTTCATAAACATATTCTGGACCTG
AAAGAATTTTTTATTCCGAAAAATGTGAGCGAACAGGCAAATCTGCTGGCAGCAAAAATT
CTGGAAAGCCAGAGCAGCCTGAGCATTCATATTCGTCGTGGCGATTATATTAAAAACAAA
ACCGCAACCCTGACACATGGTGTTTGTAGCCTGGAATATTATAAAAAAGCCCTGAACAAA
ATCCGCGATCTGGCAATGATTCGTGATGTGTTTATCTTTAGCGACGATATCTTCTGGTGC
AAAGAAAATATTGAAACCCTGCTGAGCAAAAAATATAATATTTATTATAGCGAAGATCTG
AGCCAAGAAGAGGATCTGTGGCTGATGAGCCTGGCAAATCATCATATTATTGCCAATAGC
AGCTTTAGTTGGTGGGGTGCATATCTGGGTAGCAGCGCAAGCCAGATTGTTATTTATCCG
ACCCCGTGGTATGATATTACCCCGAAAAACACCTATATCCCGATTGTGAACCATTGGATC
AACGTTGATAAACATAGCAGCTGCTAAGCGGCCGCGTCGACACGCAAAAAGGCCATCCGT
CAGGATGGCCTTCTGCTTAATTTGATGCCTGGCAGTTTATGGCGGGCGTCCTGCCCGCCA
CCCTCCGGGCCGTTGCTTCGCAACGTTCAAATCCGCTCCCGGCGGATTTGTCCTACTCAG
GAGAGCGTTCACCGACAAACAACAGATAAAACGAAAGGCCCAGTCTTTCGACTGAGCCTT
TCGTTTTATTTGATGCCTGGCAGTTCCCTACTCTCGCATGGGGAGACCCCACACTACCAT
CATGTATGAATATCCTCCTTAGTTCCTATTCCGAAGTTCCTATTCTCTAGAAAGTATAGG
AACTTCGGCGCGTCCTACCTGTGACACGCGTCAAGATCCCCTCACGCTGCCGCAAGCACT
CAGGGCGCAAGGGCTGCTAAAGGAAGCGGAACACGTAGAAAGCCAGTCCGCAGAAACGGT
GCTGACCCCGGATGAATGTCAGCTACTGGGCTATCTGGACAAGGGAAAACGCAAGCGCAA
AGAGAAAGCAGGTAGCTTGCAGTGGGCTTACATGGCGATAGCTAGACTGGGCGGTTTTAT
GGACAGCAAGCGAACCGGAATTGCCAGCTGGGGCGCCCTCTGGTAAGGTTGGGAAGCCCT
GCAAAGTAAACTGGATGGCTTTCTTGCCGCCAAGGATCTGATGGCGCAGGGGATCAAGAT
CTGATCAAGAGACAGGATGAGGATCGTTTCGCATGATTGAACAAGATGGATTGCACGCAG
GTTCTCCGGCCGCTTGGGTGGAGAGGCTATTCGGCTATGACTGGGCACAACAGACAATCG
GCTGCTCTGATGCCGCCGTGTTCCGGCTGTCAGCGCAGGGGCGCCCGGTTCTTTTTGTCA

Fig. 3 (cont.)

AGACCGACCTGTCCGGTGCCCTGAATGAACTGCAGGACGAGGCAGCGCGGCTATCGTGGC
TGGCCACGACGGGCGTTCCTTGCGCAGCTGTGCTCGACGTTGTCACTGAAGCGGGAAGGG
ACTGGCTGCTATTGGGCGAAGTGCCGGGGCAGGATCTCCTGTCATCTCACCTTGCTCCTG
CCGAGAAAGTATCCATCATGGCTGATGCAATGCGGCGGCTGCATACGCTTGATCCGGCTA
CCTGCCCATTCGACCACCAAGCGAAACATCGCATCGAGCGAGCACGTACTCGGATGGAAG
CCGGTCTTGTCGATCAGGATGATCTGGACGAAGAGCATCAGGGGCTCGCGCCAGCCGAAC
TGTTCGCCAGGCTCAAGGCGCGCATGCCCGACGGCGAGGATCTCGTCGTGACCCATGGCG
ATGCCTGCTTGCCGAATATCATGGTGGAAAATGGCCGCTTTTCTGGATTCATCGACTGTG
GCCGGCTGGGTGTGGCGGACCGCTATCAGGACATAGCGTTGGCTACCCGTGATATTGCTG
AAGAGCTTGGCGGCGAATGGGCTGACCGCTTCCTCGTGCTTTACGGTATCGCCGCTCCCG
ATTCGCAGCGCATCGCCTTCTATCGCCTTCTTGACGAGTTCTTCTGAGCGGGACTCTGGG
GTTCGAAATGACCGACCAAGCGACGCCCAACCTGCCATCACGAGATTTCGATTCCACCGC
CGCCTTCTATGAAAGGTTGGGCTTCGGAATCGTTTTCCGGGACGCCGGCTGGATGATCCT
CCAGCGCGGGGATCTCATGCTGGAGTTCTTCGCCCACCCCAGCTTCAAAAGCGCTCTCGG
TACCGGCAGGGCGGGGCGTAAGGCGCGCCATTTAAATGAAGTTCCTATTCCGAAGTTCCT
ATTCTCTAGAAAGTATAGGAACTTCGAAGCAGCTCCAG

SEQ ID No. 4
P_tet-vberc0001_9420-FRT-cat-FRT
GGCCAGATGATTAATTCCTAATTTTTGTTGACACTCTATCATTGATAGAGTTATTTTACC
ACTCCCTATCAGTGATAGAGAAAAGTGAAATGAATAGTTCGACAAAAATCTAGAAATAAT
TTTGTTTAACTTTAAGAAGGAGATATACAAATGAAGTCGGCACTGACCTTTTCCCGTCGC
ATCAATCCGGTGTTTCTGGCGTTCTTTGTCGTTGCTTTTCTGAGCGGTATCGCAGGCGCA
CTGCAGGCTCCGACCCTGAGTCTGTTTCTGTCCACGGAAGTGAAAGTTCGTCCGCTGTGG
GTTGGTCTGTTCTATACCGTCAACGCAATCGCTGGCATTACGGTTAGCTTTATCCTGGCG
AAACGTTCAGATTCGCGCGGTGACCGTCGCAAGCTGATTATGGTGTGCTATCTGATGGCG
GTTGGCAACTGTCTGCTGTTTGCCTTCAATCGTGATTACCTGACCCTGATCACGGCAGGT
GTGCTGCTGGCGAGCGTTGCCAACACCGCAATGCCGCAGATTTTCGCGCTGGCCCGTGAA
TATGCCGACAGCTCTGCACGCAAGTGGTTATGTTTAGTTCCATCATGCGCGCTCAACTG
AGTCTGGCATGGGTGATTGGTCCGCCGCTGTCCTTTATGCTGGCGCTGAATTACGGTTTT
ACCCTGATGTTCTCAATCGCGGCCGGCATTTTCGTTCTGTCGGCCCTGGTCGTGTGGTTT
ATCCTGCCGAGTGTCCCGCGTGCAGAACCGGTTGTCGATGCACCGGTGGTTGTCCAGGGT
TCACTGTTCGCAGACAAAAACGTTCTGCTGCTGTTTATCGCGTCGATGCTGATGTGGACC
TGCAATACGATGTATATTATCGATATGCCGCTGTACATTACCGCAAGCCTGGGTCTGCCG
GAACGTCTGGCTGGTCTGCTGATGGGTACCGCAGCTGGCCTGGAAATTCCGATCATGCTG
CTGGCGGGTTATTCTGTGCGTTACTTTGGCAAACGCAAGATTATGCTGTTCGCTGTTCTG
GCGGGTGTCCTGTTTTATACCGGCCTGGTTCTGTTTAAATTCAAGACGGCCCTGATGCTG
CTGCAGATCTTTAACGCAATTTTCATCGGTATTGTGGCTGGCATTGGTATGCTGTACTTC
CAAGATCTGATGCCGGGTCGTGCAGGTGCAGCAACCACGCTGTTTACCAATAGCATCTCT
ACGGGTGTCATTCTGGCAGGCGTGCTGCAAGGCGGTCTGACCGAAACGTGGGGCCATGAC
AGCGTCTATGTGATGGCGATGGTCCTGTCTATTCTGGCCCTGATTATCTGTGCACGTGTG

Fig. 3 (cont.)

CGCGAAGCTTAAATCGATACTAGCATAACCCCTTGGGGCCTCTAAACGCGTCGACACGCA
AAAAGGCCATCCGTCAGGATGGCCTTCTGCTTAATTTGATGCCTGGCAGTTTATGGCGGG
CGTCCTGCCCGCCACCCTCCGGGCCGTTGCTTCGCAACGTTCAAATCCGCTCCCGGCGGA
TTTGTCCTACTCAGGAGAGCGTTCACCGACAAACAACAGATAAAACGAAAGGCCCAGTCT
TTCGACTGAGCCTTTCGTTTTATTTGATGCCTGGCAGTTCCCTACTCTCGCATGGGGAGA
CCCCACACTACCATCATGTATGAATATCCTCCTTAGTTCCTATTCCGAAGTTCCTATTCT
CTAGAAAGTATAGGAACTTCGGCGCGTCCTACCTGTGACGGAAGATCACTTCGCAGAATA
AATAAATCCTGGTGTCCCTGTTGATACCGGGAAGCCCTGGGCCAACTTTTGGCGAAAATG
AGACGTTGATCGGCACGTAAGAGGTTCCAACTTTCACCATAATGAAATAAGATCACTACC
GGGCGTATTTTTTGAGTTGTCGAGATTTTCAGGAGCTAAGGAAGCTAAAATGGAGAAAAA
AATCACTGGATATACCACCGTTGATATATCCCAATGGCATCGTAAAGAACATTTTGAGGC
ATTTCAGTCAGTTGCTCAATGTACCTATAACCAGACCGTTCAGCTGGATATTACGGCCTT
TTTAAAGACCGTAAAGAAAAATAAGCACAAGTTTTATCCGGCCTTTATTCACATTCTTGC
CCGCCTGATGAATGCTCATCCGGAATTACGTATGGCAATGAAAGACGGTGAGCTGGTGAT
ATGGGATAGTGTTCACCCTTGTTACACCGTTTTCCATGAGCAAACTGAAACGTTTTCATC
GCTCTGGAGTGAATACCACGACGATTTCCGGCAGTTTCTACACATATATTCGCAAGATGT
GGCGTGTTACGGTGAAAACCTGGCCTATTTCCCTAAAGGGTTTATTGAGAATATGTTTTT
CGTCTCAGCCAATCCCTGGGTGAGTTTCACCAGTTTTGATTTAAACGTGGCCAATATGGA
CAACTTCTTCGCCCCCGTTTTCACCATGGGCAAATATTATACGCAAGGCGACAAGGTGCT
GATGCCGCTGGCGATTCAGGTTCATCATGCCGTTTGTGATGGCTTCCATGTCGGCAGATG
CTTAATGAATACAACAGTACTGCGATGAGTGGCAGGGCGGGGCGTAAGGCGCGCCATTTA
AATGAAGTTCCTATTCCGAAGTTCCTATTCTCTAGAAAGTATAGGAACTTC

SeqID 5

*galETKM*

TTACTCAGCAATAAACTGATATTCCGTCAGGCTGGAATACTCTTCGCCAGGACGCAGGAA
GCAGTCCGGTTGCGGCCATTCAGGGTGGTTCGGGCTGTCCGGTAGAAACTCGCTTTCCAG
AGCCAGCCCTTGCCAGTCGGCGTAAGGTTCGGTTCCCCGCGACGGTGTGCCGCCGAGGAA
GTTGCCGGAGTAGAATTGCAGAGCCGGAGCGGTGGTGTAGACCTTCAGCTGCAATTTTTC
ATCTGCTGACCAGACATGCGCCGCCACTTTCTTGCCATCGCCTTTGGCCTGTAACAAGAA
TGCGTGATCGTAACCTTTCACTTTGCGCTGATCGTCGTCGGCAAGAAACTCACTGGCGAT
GATTTTGGCGCTGCGGAAATCAAAAGACGTTCCGGCGACAGATTTCAGGCCGTCGTGCGG
AATGCCGCCTTCATCAACCGGCAGATATTCGTCCGCCAGAATCTGCAACTTGTGATTGCG
CACGTCAGACTGCTCGCCGTCAAGATTGAAATAGACGTGATTAGTCATATTCACCGGGCA
AGGTTTATCAACTGTGGCGCGATAAGTAATGGAGATACGGTTATCGTCGGTCAGACGATA
TTGCACCGTCGCGCCGAGATTACCCGGGAAGCCCTGATCACCATCATCTGAACTCAGGGC
AAACAGCACCTGACGATCGTTCTGGTTCACAATCTGCCAGCGACGTTTGTCGAACCCTTC
CGGCCCGCCGTGCAGCTGGTTAACGCCCTGACTTGGCGAAAGCGTCACGGTTTCACCGTC
AAAGGTATAACGGCTATTGGCGATACGGTTGGCATAACGACCAATAGAGGCCCCCAGAAA
CGCGGCCTGATCCTGATAGCATTCCGGGCTGGCACAGCCGAGCAGCGCCTCGCGGACGCT
GCCATCGGAAAGCGGAATACGGGCGGAAAGTAAAGTCGCACCCCAGTCCATCAGCGTGAC

Fig. 3 (cont.)

```
TACCATCCCTGCGTTGTTACGCAAAGTTAACAGTCGGTACGGCTGACCATCGGGTGCCAG
TGCGGGAGTTTCGTTCAGCACTGTCCTGCTCCTTGTGATGGTTTACAAACGTAAAAAGTC
TCTTTAATACCTGTTTTTGCTTCATATTGTTCAGCGACAGCTTGCTGTACGGCAGGCACC
AGCTCTTCCGGGATCAGCGCGACGATACAGCCGCCAAATCCGCCGCCGGTCATGCGTACG
CCACCTTTGTCGCCAATCACAGCTTTGACGATTTCTACCAGAGTGTCAATTTGCGGCACG
GTGATTTCGAAATCATCGCGCATAGAGGCATGAGACTCCGCCATCAACTCGCCCATACGT
TTCAGGTCGCCTTGCTCCAGCGCGCTGGCAGCTTCAACGGTGCGGGCGTTTTCAGTCAGT
ATATGACGCACGCGTTTTGCCACGATCGGGTCCAGTTCATGCGCAACAGCGTTGAACTCT
TCAATGGTGACATCACGCAGGGCTGGCTGCTGGAAGAAACGCGCACCGGTTTCGCACTGT
TCACGACGGGTGTTGTATTCGCTGCCAACCAGGGTACGTTTGAAGTTACTGTTGATGATG
ACGACAGCCACACCTTTGGGCATGGAAACTGCTTTGGTCCCCAGTGAGCGGCAATCGATC
AGCAAGGCATGATCTTTCTTGCCGAGCGCGGAAATTAGCTGATCCATGATCCCGCAGTTA
CAGCCTACAAACTGGTTTTCTGCTTCCTGACCGTTAAGCGCGATTTGTGCGCCGTCCAGC
GGCAGATGATAAAGCTGCTGCAATACGGTTCCGACCGCGACTTCCAGTGAAGCGGAAGAA
CTTAACCCGGCACCCTGCGGCACATTGCCGCTGATCACCATGTCCACGCCGCCGAAGCTG
TTGTTACGCAGTTGCAGATGTTTCACCACGCCACGAACGTAGTTAGCCCATTGATAGTTT
TCATGTGCGACAATGGGCGCATCGAGGGAAAACTCGTCGAGCTGATTTTCATAATCGGCT
GCCATCACGCGAACTTTACGGTCATCGCGTGGTGCACAACTGATCACGGTTTGATAATCA
ATCGCGCAGGGCAGAACGAAACCGTCGTTGTAGTCGGTGTGTTCACCAATCAAATTCACG
CGGCCAGGCGCCTGAATGGTGTGAGTGGCAGGGTAGCCAAATGCGTTGGCAAACAGAGAT
TGTGTTTTTTCTTTCAGACTCATTTCTTACACTCCGGATTCGCGAAAATGGATATCGCTG
ACTGCGCGCAAACGCTCTGCTGCCTGTTCTGCGGTCAGGTCTCGCTGGGTCTCTGCCAGC
ATTTCATAACCAACCATAAATTTACGTACGGTGGCGGAGCGCAGCAGAGGCGGATAAAAG
TGCGCGTGCAGCTGCCAGTGTTGATTCTCTTCGCCATTAAATGGCGCGCCGTGCCAGCCC
ATAGAGTAGGGGAAGGAGCACTGGAAGAGGTTGTCATAACGACTGGTCAGCTTTTTCAAC
GCCAGCGCCAGATCGCTGCGCTGGGCGTCGGTCAAATCGGTGATCCGTAAAACGTGGGCT
TTGGGCAGCAGTAGCGTTTCGAACGGCCAGGCAGCCCAGTAAGGCACGACGGCTAACCAG
TGTTCGGTTTCGACAACGGTACGGCTACCGTCTGCCAGCTCGCGCTGAACATAATCCACC
AGCATTGGTGATTTCTGTTCGGCAAAATATTCTTTTTGCAGGCGGTCTTCGCGCTCAGCT
TCGTTAGGCAGGAAGCTATTTGCCCAAATCTGACCGTGCGGATGCGGGTTAGAGCAGCCC
ATCGCCGCGCCTTTGTTTTCAAAAACCTGCACCCATGGGTACGTTTTCCCCAGTTCTGCG
GTTTGCTCCTGCCAGGTTTTGACGATTTCCGTCAATGCTGCAACGCTGAGCTCTGGCAGC
GTTTTACTGTGATCCGGTGAAAAGCAGATCACCCGGCTGGTGCCGCGCGCGCTCTGGCAA
CGCATCAGCGGATCGTGACTTTCTGGCGCATCGGCGTGTCAGACATCAAAGCCGCAAAG
TCATTAGTGAAAACGTAAGTCCCGGTGTAATCGGGGTTTTTATCGCCTGTCACCCGCACA
TTACCTGCGCAGAGGAAGCAATCTGGATCGTGCGCAGGTAACACCTGTTTGGCTGGCGTT
TCCTGCGCCCCCTGCCAGGGGCGCTTAGCGCGGTGCGGTGAAACCAGAATCCATTGCCCG
GTGAGCGGGTTGTAGCGGCGATGTGGATGATCAACGGGATTAAATTGCGTCATGGTCGTT
CCTTAATCGGGATATCCCTGTGGATGGCGTGACTGCCAGTGCCAGGTGTCCTGCGCCATT
TCATCGAGTGTGCGCGTTACGCGCCAGTTCAGTTCACGGTCGGCTTTGCTGGCGTCCGCC
CAGTAGGCCGGAAGGTCGCCCTCGCGACGCGGTGCAAAATGATAATTAACCGGTTTGCCG
CAGGCTTTGCTGAAGGCATTAACCACGTCCAGCACGCTGTTGCCTACGCCAGCGCCGAGG
```

Fig. 3 (cont.)

TTGTAGATGTGTACGCCTGGCTTGTTCGCCAGTTTTTCCATCGCCACGACGTGACCGTCC
GCCAGATCCATTACGTGGATGTAATCGCGTACGCCAGTACCATCTTCGGTCGGATAATCG
TTACCAAAAATCGCCAGCGAGTCGCGACGGCCTACAGCAACCTGGGCGATGTATGGCATC
AGGTTATTCGGAATGCCTTGCGGATCTTCGCCCATATCGCCCGACGGATGCGCGCCAACC
GGGTTGAAGTAGCGCAGCAGGGCAATGCTCCAGTCCGGCTGGGCTTTTTGCAGATCGGTG
AGGATCTGTTCCACCATCAGCTTGCTTTTGCCGTAAGGGCTTTGCGGTGTGCCGGTCGGG
AAGCTTCAACGTATGGAATTTTGGGCTGATCGCCATAAACGGTGGCGGAGGAGCTAAAA
ATAAAGTTTTTGACGTTAGCGGCGCGCATGGCGCTAATCAGGCGCAGAGTGCCGTTGACA
TTGTTGTCGTAATATTCCAGCGGTTTTTGTACCGATTCGCCCACGGCTTTCAGCCCGGCG
AAGTGGATCACGGTGTCGATAGCGTGATCGTGCAGGATCTCGGTCATCAACGCTTCGTTA
CGAATATCGCCTTCAACAAACGTTGGATGTTTGCCGCCTAAACGCTCGATAACAGGCAGT
ACGCTGCGCTTACTGTTACAGAGGTTATCAAGAATGATGACATCATGACCGTTTTGCAGT
AATTGCACACAGGTATGACTTCCAATGTAACCGCTACCACCGGTAACCAGAACTCTCAT

SEQ ID No. 6

*Ptet-fkp-lox-aacC1-lox*

TGGCCAGATGATTAATTCCTAATTTTTGTTGACACTCTATCATTGATAGAGTTATTTTAC
CACTCCCTATCAGTGATAGAGAAAAGTGAAATGAATAGTTCGACAAAAATCTAGAAATAA
TTTTGTTTAACTTTAAGAAGGAGATATACAAATGCAAAAACTACTATCTTTACCGTCCAA
TCTGGTTCAGTCTTTTCATGAACTGGAGAGGGTGAATCGTACCGATTGGTTTTGTACTTC
CGACCCGGTAGGTAAGAAACTTGGTTCCGGTGGTGGAACATCCTGGCTGCTTGAAGAATG
TTATAATGAATATTCAGATGGTGCTACTTTTGGAGAGTGGCTTGAAAAAGAAAAAGAAT
TCTTCTTCATGCGGGTGGGCAAAGCCGTCGTTTACCCGGCTATGCACCTTCTGGAAAGAT
TCTCACTCCGGTTCCTGTGTTCCGGTGGGAGAGAGGGCAACATCTGGGACAAAATCTGCT
TTCTCTGCAACTTCCCCTATATGAAAAAATCATGTCTTTGGCTCCGGATAAACTCCATAC
ACTGATTGCGAGTGGTGATGTCTATATTCGTTCGGAGAAACCTTTGCAGAGTATTCCCGA
AGCGGATGTGGTTTGTTATGGACTGTGGGTAGATCCGTCTCTGGCTACCCATCATGGCGT
GTTTGCTTCCGATCGCAAACATCCCGAACAACTCGACTTTATGCTTCAGAAGCCTTCGTT
GGCAGAATTGGAATCTTTATCGAAGACCCATTTGTTCCTGATGGACATCGGTATATGGCT
TTTGAGTGACCGTGCCGTAGAAATCTTGATGAAACGTTCTCATAAAGAAAGCTCTGAAGA
ACTAAAGTATTATGATCTTTATTCCGATTTTGGATTAGCTTTGGGAACTCATCCCCGTAT
TGAAGACGAAGAGGTCAATACGCTATCCGTTGCTATTCTGCCTTTGCCGGGAGGAGAGTT
CTATCATTACGGGACCAGTAAAGAACTGATTTCTTCAACTCTTTCCGTACAGAATAAGGT
TTACGATCAGCGTCGTATCATGCACCGTAAAGTAAAGCCCAATCCGGCTATGTTTGTCCA
AAATGCTGTCGTGCGGATACCTCTTTGTGCCGAGAATGCTGATTTATGGATCGAGAACAG
TCATATCGGACCAAAGTGGAAGATTGCTTCACGACATATTATTACCGGGGTTCCGGAAAA
TGACTGGTCATTGGCTGTGCCTGCCGGAGTGTGTGTAGATGTGGTTCCGATGGGTGATAA
GGGCTTTGTTGCCCGTCCATACGGTCTGGACGATGTTTTCAAAGGAGATTTGAGAGATTC
CAAAACAACCCTGACGGGTATTCCTTTTGGTGAATGGATGTCCAAACGCGGTTTGTCATA
TACAGATTTGAAAGGACGTACGGACGATTTACAGGCAGTTTCCGTATTCCCTATGGTTAA
TTCTGTAGAAGAGTTGGGATTGGTGTTGAGGTGGATGTTGTCCGAACCCGAACTGGAGGA

AGGAAAGAATATCTGGTTACGTTCCGAACATTTTTCTGCGGACGAAATTTCGGCAGGTGC
CAATCTGAAGCGTTTGTATGCACAACGTGAAGAGTTCAGAAAAGGAAACTGGAAAGCATT
GGCCGTTAATCATGAAAAAAGTGTTTTTTATCAACTTGATTTGGCCGATGCAGCTGAAGA
TTTTGTACGTCTTGGTTTGGATATGCCTGAATTATTGCCTGAGGATGCTCTGCAGATGTC
ACGCATCCATAACCGGATGTTGCGTGCGCGTATTTTGAAATTAGACGGGAAAGATTATCG
TCCGGAAGAACAGGCTGCTTTTGATTTGCTTCGTGACGGCTTGCTGGACGGGATCAGTAA
TCGTAAGAGTACCCCAAAATTGGATGTATATTCCGATCAGATTGTTTGGGGACGTAGCCC
CGTGCGCATCGATATGGCAGGTGGATGGACCGATACTCCTCCTTATTCACTTTATTCGGG
AGGAAATGTGGTGAATCTAGCCATTGAGTTGAACGGACAACCTCCCTTACAGGTCTATGT
GAAGCCGTGTAAAGACTTCCATATCGTCCTGCGTTCTATCGATATGGGTGCTATGGAAAT
AGTATCTACGTTTGATGAATTGCAAGATTATAAGAAGATCGGTTCACCTTTCTCTATTCC
GAAAGCCGCTCTGTCATTGGCAGGCTTTGCACCTGCGTTTTCTGCTGTATCTTATGCTTC
ATTAGAGGAACAGCTTAAAGATTTCGGTGCAGGTATTGAAGTGACTTTATTGGCTGCTAT
TCCTGCCGGTTCCGGTTTGGGCACCAGTTCCATTCTGGCTTCTACCGTACTTGGTGCCAT
TAACGATTTCTGTGGTTTAGCCTGGGATAAAAATGAGATTTGTCAACGTACTCTTGTTCT
TGAACAATTGCTGACTACCGGAGGTGGATGGCAGGATCAGTATGGAGGTGTGTTGCAGGG
TGTGAAGCTTCTTCAGACCGAGGCCGGCTTTGCTCAAAGTCCATTGGTGCGTTGGCTACC
CGATCATTTATTTACGCATCCTGAATACAAAGACTGTCACTTGCTTTATTATACCGGTAT
AACTCGTACGGCAAAAGGGATCTTGGCAGAAATAGTCAGTTCCATGTTCCTCAATTCATC
GTTGCATCTCAATTTACTTTCGGAAATGAAGGCGCATGCATTGGATATGAATGAAGCTAT
ACAGCGTGGAAGTTTTGTTGAGTTTGGCCGTTTGGTAGGAAAAACCTGGGAACAAAACAA
AGCATTGGATAGCGGAACAAATCCTCCGGCTGTGGAGGCAATTATCGATCTGATAAAAGA
TTATACCTTGGGATATAAATTGCCGGGAGCCGGTGGTGGCGGGTACTTATATATGGTAGC
GAAAGATCCGCAAGCTGCTGTTCGTATTCGTAAGATACTGACAGAAAACGCTCCGAATCC
GCGGGCACGTTTTGTCGAAATGACGTTATCTGATAAGGGATTCCAAGTATCACGATCATA
ACTGAAACCAATTTGCCTGGCGGCAGTAGCGCGGTGGTCCCACCTGACCCCATGCCGAAC
TCAGAAGTGAAACGCCGTAGCGCCGATGGTAGTGTGGGGTCTCCCCATGCGAGAGTAGGG
AACTGCCAGGCATCAAATAAAACGAAAGGCTCAGTCGAAAGACTGGGCCTTTCGGGATCC
AGGCCGGCCTGTTAAGACGGCCAGTGAATTCGAGCTCGGTACCTACCGTTCGTATAATGT
ATGCTATACGAAGTTATCGAGCTCTAGAATGATCCCCTCATTAGGCCACACGTTCAAG
TGCAGCGCACACCGTGGAAACGGATGAAGGCACGAACCCAGTTGACATAAGCCTGTTCGG
TTCGTAAACTGTAATGCAAGTAGCGTATGCGCTCACGCAACTGGTCCAGAACCTTGACCG
AACGCAGCGGTGGTAACGGCGCAGTGGCGGTTTTCATGGCTTGTTATGACTGTTTTTTTG
TACAGTCTATGCCTCGGGCATCCAAGCAGCAAGCGCGTTACGCCGTGGGTCGATGTTTGA
TGTTATGGAGCAGCAACGATGTTACGCAGCAGCAACGATGTTACGCAGCAGGGCAGTCGC
CCTAAAACAAAGTTAGGTGGCTCAAGTATGGGCATCATTCGCACATGTAGGCTCGGCCCT
GACCAAGTCAAATCCATGCGGGCTGCTCTTGATCTTTTCGGTCGTGAGTTCGGAGACGTA
GCCACCTACTCCCAACATCAGCCGGACTCCGATTACCTCGGGAACTTGCTCCGTAGTAAG
ACATTCATCGCGCTTGCTGCCTTCGACCAAGAAGCGGTTGTTGGCGCTCTCGCGGCTTAC
GTTCTGCCCAGGTTTGAGCAGCCGCGTAGTGAGATCTATATCTATGATCTCGCAGTCTCC
GGCGAGCACCGGAGGCAGGGCATTGCCACCGCGCTCATCAATCTCCTCAAGCATGAGGCC
AACGCGCTTGGTGCTTATGTGATCTACGTGCAAGCAGATTACGGTGACGATCCCGCAGTG

Fig. 3 (cont.)

GCTCTCTATACAAAGTTGGGCATACGGGAAGAAGTGATGCACTTTGATATCGACCCAAGT
ACGCCACCTAACAATTCGTTCAAGCCGAGATCGTAGAATTTCGACGACCTGCAGCCAAG
CATAACTTCGTATAATGTATGCTATACGAACGGTAGGATCCTCTAGAGTCGACCTGCAGG
CATGAGATGTGTATAAGAGACAG

SEQ ID No. 7

*P_ter-fbaB-P_T7-His_6-fbpase-lox-aacC1-lox*

GGGAATTGATTCTGGTACCAAATGAGTCGACCGGCCAGATGATTAATTCCTAATTTTTGT
TGACACTCTATCATTGATAGAGTTATTTTACCACTCCCTATCAGTGATAGAGAAAAGTGA
AATGAATAGTTCGACAAAAATCTAGAAATAATTTTGTTTAACTTTAAGAAGGAGATATAC
AAATGATTACCCGCAAAAGGCGGGCCAGGACAATCCATAGCCGATATCCAATCGGAATTT
ACGGGAGCATAGTAATGACAGATATTGCACAGTTGCTTGGCAAAGACGCCGACAACCTTT
TACAGCACCGTTGTATGACTATTCCTTCTGACCAGCTTTATCTCCCCGGACATGACTACG
TAGACCGCGTGATGATTGACAATAATCGCCCGCCAGCGGTGTTACGTAATATGCAGACGT
TGTACAACACTGGGCGTCTGGCTGGCACAGGATATCTTTCTATTCTGCCGGTTGACCAGG
GCGTTGAGCACTCTGCCGGAGCTTCATTTGCTGCTAACCCGCTCTACTTTGACCCGAAAA
ACATTGTTGAACTGGCGATCGAAGCGGGCTGTAACTGTGTGGCATCAACTTACGGCGTGT
TGGCGTCGGTATCGCGGCGCTATGCGCATCGCATTCCATTCCTCGTCAAACTTAATCACA
ACGAGACGCTAAGTTACCCGAACACCTACGATCAAACGCTGTATGCCAGCGTGGAGCAGG
CCTTCAACATGGGCGCGGTGGCGGTTGGTGCGACTATCTATTTTGGTTCGGAAGAGTCAC
GTCGCCAGATTGAAGAAATTTCTGCGGCTTTTGAACGTGCGCACGAGCTGGGCATGGTGA
CAGTGCTGTGGGCCTATTTGCGTAACTCCGCCTTTAAGAAAGATGGCGTTGATTACCATG
TTTCCGCCGACCTGACCGGTCAGGCAAACCATCTGGCGGCGACCATAGGTGCAGATATCG
TCAAACAAAAATGGCGGAAAATAACGGCGGCTATAAAGCAATTAATTACGGTTATACCG
ACGATCGCGTGTACAGCAAGTTAACCAGCGAAAACCCGATTGATCTGGTGCGTTATCAGT
TAGCTAACTGCTATATGGGCCGGGCCGGGTTGATAAACTCCGGCGGTGCTGCAGGCGGTG
AAACTGACCTCAGCGATGCAGTGCGTACTGCGGTTATCAACAAACGCGCTGGCGGAATGG
GGCTGATTCTTGGACGTAAGGCGTTCAAGAAATCGATGGCTGACGGCGTGAAACTGATTA
ACGCCGTGCAGGATGTTTATCTCGATAGCAAAATTACTATCGCCTAAGAGGATCGAGATC
TCGATCCCGCGAAATTAATACGACTCACTATAGGGGAATTGTGAGCGGATAACAATTCCC
CTCTAGAAATAATTTTGTTTAACTTTAAGAAGGAGATATACCATGGGCCATCATCATCAT
CATCATCATCATCACAGCAGCGGCCATATCGAAGGTCGTCATATGGCGGTGAAAGAA
GCGACCAGCGAGACCAAGAAGCGTAGCGGTTACGAGATCATTACCCTGACCAGCTGGCTG
CTGCAACAAGAACAGAAGGGTATCATTGACGCGGAACTGACCATCGTTCTGAGCAGCATT
AGCATGGCGTGCAAACAGATCGCGAGCCTGGTGCAACGTGCGAACATTAGCAACCTGACC
GGTACCCAAGGCGCGGTTAACATCCAGGGTGAAGACCAAAAGAAACTGGATGTTATTAGC
AACGAGGTGTTCAGCAACTGCCTGCGTAGCAGCGGTCGTACCGGCATCATTGCGAGCGAG
GAAGAGGACGTGGCGGTTGCGGTGGAAGAGAGCTACAGCGGTAACTATATCGTGGTTTTT
GACCCGCTGGATGGCAGCAGCAACCTGGATGCGGCTGTGAGCACCGGTAGCATCTTCGGC
ATTTACAGCCCGAACGACGAGAGCCTGCCGGATTTTGGTGACGATAGCGACGATAACACC
CTGGGCACCGAAGAGCAACGTTGCATCGTTAACGTGTGCCAACCGGGTAGCAACCTGCTG

```
GCGGCGGGCTACTGCATGTATAGCAGCAGCGTTGCGTTCGTGCTGACCATTGGCAAGGGC
GTTTTCGTGTTTACCCTGGACCCGCTGTACGGTGAATTCGTGCTGACCCAGGAGAACCTG
CAAATCCCGAAGAGCGGTGAAATTTACAGCTTTAACGAGGGCAACTATAAACTGTGGGAT
GAAAACCTGAAGAAATATATCGACGATCTGAAGGAACCGGGTCCGAGCGGTAAACCGTAC
AGCGCGCGTTATATCGGTAGCCTGGTTGGCGACTTCCACCGTACCCTGCTGTACGGTGGC
ATTTACGGTTATCCGCGTGATAAGAAAAGCAAGAACGGCAAACTGCGTCTGCTGTATGAA
TGCGCGCCGATGAGCTTTATTGTTGAGCAGGCGGGTGGCAAAGGTAGCGACGGCCACCAG
CGTGTGCTGGATATCCAACCGACCGAAATTCACCAGCGTGTTCCGCTGTACATTGGTAGC
ACCGAAGAGGTTGAAAAAGTTGAAAAGTATCTGGCGTAATCGAGTCTGGTAAAGAAACCG
CTGCTGCGAAATTTGAACGCCAGCACATGGACTCGTCTACTAGCGCAGCTTAATTAACCT
AGGCTGCTGCCACCGCTGAGCAATAACTAGCATAACCCCTTGGGGCCTCTAAACGGGTCT
TGAGGGGTTTTTTGCTGAAAGGAGGAACTATATCCGGATTGGCGAATGGGACGCGCCCTG
TAGCGGCGCATTAAGCGCGGCGGGTGGACGGCCAGTGAATTCGAGCTCGGTACCTACCGT
TCGTATAATGTATGCTATACGAAGTTATCGAGCTCTAGAGAATGATCCCCTCATTAGGCC
ACACGTTCAAGTGCAGCGCACACCGTGGAAACGGATGAAGGCACGAACCCAGTTGACATA
AGCCTGTTCGGTTCGTAAACTGTAATGCAAGTAGCGTATGCGCTCACGCAACTGGTCCAG
AACCTTGACCGAACGCAGCGGTGGTAACGGCGCAGTGGCGGTTTTCATGGCTTGTTATGA
CTGTTTTTTTGTACAGTCTATGCCTCGGGCATCCAAGCAGCAAGCGCGTTACGCCGTGGG
TCGATGTTTGATGTTATGGAGCAGCAACGATGTTACGCAGCAGCAACGATGTTACGCAGC
AGGGCAGTCGCCCTAAAACAAAGTTAGGTGGCTCAAGTATGGGCATCATTCGCACATGTA
GGCTCGGCCCTGACCAAGTCAAATCCATGCGGGCTGCTCTTGATCTTTTCGGTCGTGAGT
TCGGAGACGTAGCCACCTACTCCCAACATCAGCCGGACTCCGATTACCTCGGGAACTTGC
TCCGTAGTAAGACATTCATCGCGCTTGCTGCCTTCGACCAAGAAGCGGTTGTTGGCGCTC
TCGCGGCTTACGTTCTGCCCAGGTTTGAGCAGCCGCGTAGTGAGATCTATATCTATGATC
TCGCAGTCTCCGGCGAGCACCGGAGGCAGGGCATTGCCACCGCGCTCATCAATCTCCTCA
AGCATGAGGCCAACGCGCTTGGTGCTTATGTGATCTACGTGCAAGCAGATTACGGTGACG
ATCCCGCAGTGGCTCTCTATACAAAGTTGGGCATACGGGAAGAAGTGATGCACTTTGATA
TCGACCCAAGTACCGCCACCTAACAATTCGTTCAAGCCGAGATCGTAGAATTTCGACGAC
CTGCAGCCAAGCATAACTTCGTATAATGTATGCTATACGAACGGTAGGATCCTCTAGAGT
CGACCTGCAGGC
```

PROCESS FOR THE PRODUCTION OF FUCOSYLATED OLIGOSACCHARIDES

CROSS-REFERENCE TO RELATED APPLICATIONS

This application is a National Stage entry of International Application No. PCT/EP2017/077192, filed 24 Oct. 2017, which claims priority to European Patent Application No. 16196486.1, filed 29 Oct. 2016.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000045-007000_ST25.txt" created on 26 Apr. 2019, and 37,207 bytes in size) is submitted concurrently with the instant application, and the entire contents of the Sequence Listing are incorporated herein by reference.

The present invention relates to a method for the production of fucosylated oligosaccharides using a genetically modified prokaryotic host cell, as well as to a host cell employed in this method and its use for producing fucosylated oligosaccharides to high titers.

BACKGROUND OF THE INVENTION

Human milk represents a complex mixture of carbohydrates, fats, proteins, vitamins, minerals and trace elements. The by far most predominant fraction is represented by carbohydrates, which can be further divided into lactose and more complex oligosaccharides (Human milk oligosaccharides, HMO). Whereas lactose is used as an energy source, the complex oligosaccharides are not metabolized by the infant. The fraction of complex oligosaccharides accounts for up to 20% of the total carbohydrate fraction and consists of more than 200 different oligosaccharides. The occurrence and concentration of these complex oligosaccharides are specific to humans and thus cannot be found in large quantities in the milk of other mammals.

Approximately 200 structurally-diverse HMOs have been identified so far and numerous beneficial properties have been reported. HMOs are not digested by breastfed infants, but represent a valuable carbon and energy source for beneficial bacteria of the genera *Bifidobacteria, Lactobacillus* and *Bacteroides* in the intestine, causing them to become dominant in the gut and allowing them to outcompete pathogens, thus preventing infections of the gut epithelium. However, HMOs also bind directly to pathogenic bacteria, protozoa and viruses, blocking pathogen-host interactions by mimicking glycan cell surface receptors and thereby protecting the breastfed child from infectious diseases.

The most prominent oligosaccharide is 2'-fucosyllactose. Further prominent HMOs present in human milk are 3-fucosyllactose, lacto-N-tetraose, lacto-N-neotetraose and the lacto-N-fucopentaoses. Besides these neutral oligosaccharides, also acidic HMOs can be found in human milk, like for e.g. 3'-sialyllactose, 6'-sialyllactose and sialyllacto-N-tetraose a, b, and c, or sialyllacto-N-fucpentaose II etc. These structures are closely related to epitopes of epithelial cell surface glycoconjugates, the Lewis histoblood group antigens, and the structural homology of HMO to epithelial epitopes accounts for protective properties against bacterial pathogens.

Due to their beneficial properties, HMOs are favored for inclusion as ingredients in infant formulae and other food products, necessitating the production of HMOs in large quantities, up to the multi-ton scale.

Due to the limited supply and difficulties of obtaining pure fractions of individual human milk oligosaccharides, chemical routes to some of these complex molecules were developed. However, chemical and biocatalytic approaches proved to be not commercially sustainable, and, furthermore, particularly chemical synthetic routes to human milk oligosaccharides involve several noxious chemicals, which impose the risk to contaminate the final product.

Due to the challenges involved in the chemical synthesis of human milk oligosaccharides, several enzymatic methods and fermentative approaches were developed. Today, for several HMOs such as 2'-fucosyllactose, 3-fucosyllactose, lacto-N-tetraose, lacto-N-neotetraose, lacto-N-fucopentaose I, lacto-N-difucohexaose II, 3'-sialyllactose and 6'-sialyllactose fermentative approaches have been developed, using mainly genetically engineered bacterial strains such as recombinant *Escherichia coli*.

However, even the most efficient processes based on bacterial fermentation, which are available today, do not or hardly achieve HMO titers greater than 20 g/L in the culture broth. Industrial-scale processes must typically exceed titers of 50 g/L although 100 g/L is more desirable.

Thus, it is an object of the present invention to provide for an improved fermentation process by means of which a biosynthesis of fucosylated oligosaccharides, in particular of 2'-fucosyllactose, is enabled at a titer exceeding more than 100 g/L.

SUMMARY OF THE INVENTION

This, and other objects are solved by a method for the production of fucosylated oligosaccharides using a genetically modified prokaryotic host cell, the method comprising the steps of:
providing a host cell, which has been genetically modified, such, that at least (i) the activity of a fructose-6-phosphate-converting enzyme, which in the unmodified host cell has a regular level, is lowered or abolished; (ii) at least one gene encoding an enzyme necessary for the de novo synthesis of GDP-fucose is overexpressed in the host cell; (iii) an exogenous gene, encoding a fucosyltransferase, preferably an alpha-1,2-fucosyltransferase and/or alpha-1,3-fucosyltransferase, is expressed, preferably overexpressed, in the host cell;
cultivating said genetically modified host cell in a cultivation medium containing a carbon and energy source that is selected from at least one of the following: glucose, sucrose, glycerol, succinate, citrate, pyruvate, malate, lactate, or ethanol; and
providing lactose to the cultivation medium with lactose.

In a subsequent step, the thus produced fucosylated oligosaccharide may be retrieved or obtained from the medium the host cell is cultivated in.

The step of growing and cultivating the genetically modified host cell and the step of adding lactose to the cultivation medium can be performed such, that the genetically modified host cell is first cultivated for a certain period of time, and, in a subsequent step after this first cultivation time, lactose is provided by adding it to the medium the host cell is cultivated in; alternatively, lactose may be provided from the beginning of the cultivation time of the genetically modified host cell, in a certain amount, and may be constantly added in a certain amount. Alternatively, lactose can be generated internally.

The object is further solved by a genetically modified prokaryotic host cell and by its use for the production of a fucosylated oligosaccharide, which host cell has been genetically modified such, that at least (i) the activity of a fructose-6-phosphate-converting enzyme, which in the unmodified host cell is at a regular level, is lowered or abolished and/or by having increased the activity of a fructose-6-phosphate generating enzyme in the host cell; (ii) at least one gene encoding an enzyme necessary for the de novo synthesis of GDP-fucose is overexpressed; (iii) an exogenous gene encoding a fucosyltransferase, preferably an alpha-1,2-fucosyltransferase and/or alpha-1,3-fucosyltransferase, is expressed, preferably overexpressed, in the host cell.

Optionally, the host cell has been genetically further modified (iv) to express a gene encoding a protein enabling or facilitating the transport of the desired fucosylated oligosaccharide into the medium the host cell is cultivated in; and/or (v) to express an exogenous gene encoding a bifunctional L-fucokinase/L-fucose 1-phosphate guanylyltransferase; and/or (vi) to have inactivated or deleted genes encoding a L-fucose-isomerase and L-fuculose-kinase; and/or (vii) to have inactivated or disrupted genes coding for enzymes of the colanic acid synthesis; and/or (viii) to express a lactose permease; and/or (ix) to have inactivated or deleted endogenous beta-galactosidase genes; and/or (x) to express an exogenous regulable beta-galactosidase gene; and/or (xi) to overexpress exogenous genes for metabolizing galactose, and/or (xii) to express an exogenous gene encoding an enzyme exhibiting fructose-1,6-bisphosphate phosphatase activity.

Also, herein provided is a method for the production of fucosylated oligosaccharides using a genetically modified prokaryotic host cell, the method comprising the steps of:
  providing a prokaryotic host cell, which has been genetically modified, such, that at least (i) the fructose-6-phosphate pool in said genetically modified host cell is increased by having lowered or abolished the activity of a fructose-6-phosphate-converting enzyme, which in the unmodified host cell has a regular level, or by having increased the activity of a fructose-6-phosphate generating enzyme; that (ii) at least one gene encoding an enzyme necessary for the de novo synthesis of GDP-fucose is overexpressed in the host cell; (iii) an exogenous gene encoding an alpha-1,2-fucosyltransferase and/or alpha-1,3-fucosyltransferase is expressed in the host cell;
  cultivating said genetically modified host cell in a cultivation medium containing a carbon and energy source that is selected from at least one of the following: glucose, sucrose, glycerol, succinate, citrate, pyruvate, malate, lactate, or ethanol; and
  providing lactose to the cultivation medium with lactose.

The objects underlying the invention are completely solved in this way.

With the method according to the invention, as well as with the genetically modified host cell employed in the method, it is possible to produce fucosylated oligosaccharides at a titer exceeding 50 g/L, and even 100 g/L, and even more 150 g/L, thus providing a successful tool for the large-scale and, thus, industrial-scale fermentative production of fucosylated oligosaccharides.

Presently, and as generally understood in the state of the art, a "fucosylated oligosaccharide" is a fucosylated oligosaccharide as found in human milk, i.e. an oligosaccharide that is carrying a fucose-residue. Preferably, the fucosylated oligosaccharide is one that is selected from 2'-fucosyllactose, 3-fucosyllactose or difucosyllactose.

Also, a "genetically modified prokaryotic host cell" presently means a prokaryotic cell whose genetic material has been altered using genetic engineering techniques. E.g., the host cell has been genetically modified, such, that either endogenous nucleic sequences naturally occurring in said host cell have been deleted, interrupted or otherwise influenced so that their expression is modified, i.e. abolished, lowered, suppressed, enhanced, or similar, and/or exogenous nucleic acids, i.e. nucleic acids that are foreign to said host cell, have been introduced into the host cell to be expressed, e.g. under control of an controllable promoter, in the host cell. In this connection, such genetically modified host cells are also called "recombinant host cells". For example, a subject prokaryotic host cell is a genetically modified prokaryotic host cell, by virtue of introduction into a suitable prokaryotic host cell a heterologous nucleic acid, e.g., an exogenous nucleic acid that is foreign to the prokaryotic host cell, or a recombinant nucleic acid that is not normally found in the prokaryotic host cell.

Accordingly, the term "recombinant", as used herein with reference to a bacterial host cell indicates that the bacterial cell replicates a heterologous nucleic acid, or expresses a peptide or protein encoded by a heterologous nucleic acid (i.e., a sequence "foreign to said cell"). Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. Accordingly, a "recombinant polypeptide" is one which has been produced by a recombinant cell. A "heterologous sequence" or a "heterologous nucleic acid", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microorganism cell, wherein techniques may be applied which will depend on the host cell and the sequence that is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989).

Accordingly, a "genetically modified prokaryotic host cell" is presently understood as a prokaryotic cell which has been transformed or transfected, or is capable of transformation or transfection by an exogenous polynucleotide sequence.

The nucleic acid sequences as used in the present invention, may, e.g., be comprised in a vector which is to be stably transformed/transfected or otherwise introduced into host microorganism cells.

A great variety of expression systems can be used to express the genes in the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesize a polypeptide in a host may be used for expression in this regard. The appropriate DNA sequence may be inserted into the expression system by any of a variety of well-known and routine techniques, such as, for example, those set forth in Sambrook et al., supra.

The art is rich in patent and literature publications relating to "recombinant DNA" methodologies for the isolation, synthesis, purification and amplification of genetic materials for use in the transformation of selected host organisms. Thus, it is common knowledge to transform host organisms with "hybrid" viral or circular plasmid DNA which includes selected exogenous (i.e. foreign or "heterologous") DNA sequences. A person skilled in the art will know a variety of methods to achieve "hybrid" vectors for use in the transformation of a selected host organism.

The term "nucleic acid sequence encoding . . . " generally refers to any polyribonucleotide or polydeoxyribonucleotide, which may be unmodified RNA or DNA or modified RNA or DNA, and generally represents a gene which encodes a certain polypeptide or protein. The term includes, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

As used herein, the term "cultivating" means growing and/or incubating a bacterial cell in a medium and under conditions permissive and suitable for the production of the desired oligosaccharide(s). A couple of suitable bacterial host cells as well as mediums and conditions for their cultivation will be readily available for one skilled in the art upon reading the disclosure of this invention in connection with the skilled person's technical and expert background.

It is to be understood that with the invention as disclosed herein, the production of one or more oligosaccharides as defined herein is possible, as long as the respective nucleic acids encoding the relevant proteins/enzymes as disclosed herein are comprised in the cell(s).

As used herein, the term "recovering" means isolating, harvesting, purifying, collecting or otherwise separating from the host microorganism culture the oligosaccharide produced by the host microorganism according to the invention.

According to an embodiment of the method and the use of the invention, the fucosylated oligosaccharide to be produced is selected from at least one of 2'-fucosyllactose, 3-fucosyllactose or difucosyllactose.

According to an embodiment of the method of the invention, the prokaryotic host cell is selected from the group consisting of bacterial host cells, preferably selected from an *Escherichia coli* strain, a *Lactobacillus* species, or a *Corynebacterium glutamicum* strain.

Preferably, the host cell is a bacterial host cell selected from an *Escherichia coli*, *Corynebacterium glutamicum*, *Bacillus subtilis*, *Bacillus megaterium*, *Lactobacillus casei*, *Lactobacillus acidophilus*, *Lactobacillus helveticus*, *Lactobacillus delbrueckii*, *Lactococcus lactis* cell. A person skilled in the art will be aware of further bacterial strains when reading the present disclosure.

Presently, and as generally understood, the expression "fucosyltransferase" is understood as an enzyme that transfers an L-fucose sugar from a GDP-fucose (guanosine diphosphate-fucose) donor substrate to an acceptor substrate to form the fucosylated oligosaccharide. The acceptor substrate, in the present invention, is an oligosaccharide. Also, fucosyltransferases not only catalyze fucosylation in the presence of glycan acceptors, but can also hydrolyze GDP-L-fucose when no acceptor substrate is available.

Accordingly, the terms "alpha-1,2-fucosyltransferase" or "fucosyltransferase" or a nucleic acid/polynucleotide encoding an "alpha-1,2-fucosyltranferase" or "fucosyltransferase" refer to a glycosyltransferase that catalyzes the transfer of the fucose moiety from a donor substrate, for example, GDP-fucose, to an acceptor molecule in an alpha-1,2-linkage. The terms "alpha-1,3-fucosyltranferase" or "fucosyltransferase" or a nucleic acid/polynucleotide encoding an "alpha-1,3-fucosyltranferase" or "fucosyltransferase" refer to a glycosyltransferase that catalyzes the transfer of the fucose moiety from a donor substrate, for example, GDP-fucose, to an acceptor molecule in an alpha-1,3-linkage. The acceptor molecule can be, e.g., lactose, 2'-fucosyllactose, 3-fucosyllactose, 3'-sialyllactose, 6'-sialyllactose, lacto-N-tetraose, lacto-N-neotetraose or a derivative thereof.

According to the invention, the exogenous gene encoding a fucosyltransferase is selected from a gene expressing a protein exhibiting an alpha-1,2-fucosyltransferase activity, a gene expressing a protein exhibiting an alpha-1,3-fucosyltransferase activity, or a gene expressing an alpha-1,2-fucosyltransferase as well as an alpha-1,3-fucosyltransferase activity.

According to preferred embodiments, for the synthesis of 2'-fucosyllactose a suitable alpha-1,2-fucosyltransferase is expressed, for the synthesis of 3-fucosyllactose a suitable alpha-1,3-fucosyltransferase is expressed, for the synthesis of 2',3-difucosyllactose, both, a suitable alpha-1,2-fucosyltransferase and an alpha-1,3-fucosyltransferase or at least one gene encoding for a protein exhibiting an alpha-1,2- as well as an alpha-1,3-fucosyltransferase activity is expressed.

Non-limiting examples for fucosyltransferases which can be used according to the invention and which shall be part of the invention are, e.g., bacterial fucosyltransferases, and preferably an alpha-1,2-fucosyltransferase, and more preferably the alpha-1,2-fucosyltransferase encoded by the wbgL gene of *E. coli*:O126, or the alpha-1,2-fucosyltransferase encoded by the fucT gene of *Helicobacter pylori*, or an alpha-1,3-fucosyltransferase, and more preferably an alpha-1,3-fucosyltransferase from *Akkermansia muciniphila*, *Bacteroides fragilis*, *H. pylori*, or *H. hepaticus*. Preferably, a glycosyltransferase is used or variants thereof which is disclosed in EP 2 479 263 A1 or from EP 2 439 264 or in WO 2010/142305, the content of which is herewith explicitly referred to and made subject matter of this invention.

A "variant" as the term is used herein, is a polynucleotide or polypeptide that differs from a reference polynucleotide or polypeptide, in particular an enzyme as mentioned and used herein, respectively, but retains the essential (enzymatic) properties of the reference polynucleotide or polypeptide. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

Within the scope of the present invention, also nucleic acid/polynucleotide and polypeptide polymorphic variants, alleles, mutants, and interspecies homologs are comprised by those terms, that have an amino acid sequence/nucleic acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide as mentioned herein, e.g. to an fructose-6-phosphate-converting enzyme, in particular phosphofructokinase A, glucose-6-phosphate isomerase, fructose-6-phosphate aldolase, a transketolase, e.g. tktA, tktB, or a transaldolase, e.g. talA, talB, a fructose-1,6-bisphosphate phosphatase, as used herein, to the phosphomannomutase, preferably manB, a mannose-1-phosphate guanosyltransferase, preferably manC, a GDP-mannose-4,6-dehydratase, preferably gmd, and a GDP-L-fucose synthase, preferably wcaG, to a fucosyltransferase as used herein, to a fructose-1,6-bisphosphate phosphatase, preferably the functional active variant of the fructose-1,6-bisphosphate phosphatase (fbpase) from *Pisum sativum*, to the sugar efflux transporter, e.g. yberc0001_9420 or SetA, and to the lactose permease, e.g. LacY, used herein.

Accordingly, a "functional fragment" of any of the genes/proteins disclosed therein, is meant to designate sequence variants of the genes/proteins still retaining the same or somewhat lesser activity of the gene or protein the respective fragment is derived from.

As defined herein, the term "endogenous" herein and generally within the field means that the nucleic acid encoding for an enzyme of interest is originating from the bacterial host cell and has not been introduced into said host cell, whereas an "exogenous" or "recombinant" nucleic acid has been introduced into said host cell and does not originate from said host cell.

According to another embodiment, the nucleic acid/gene is homologous or heterologous. Presently, and as generally understood in the relevant field, the expression "homologous" refers to a nucleic acid sequence/gene that encodes for a specific product or products and is derived from the same species, in which said nucleic acid sequence is inserted. Accordingly, the term "heterologous" refers to a nucleic acid sequence/gene encoding for a specific product or products and being derived from a species other than those in which said nucleic acid sequence/gene is inserted.

According to another embodiment, the host cell of the invention further comprises control sequences enabling the controlled overexpression of endogenous or exogenous/recombinant nucleic acid sequences/genes. As defined above, the term "control sequence" which herein is synonymously used with the expression "nucleic acid/gene expression control sequence", comprises promoter sequences, signal sequence, or array of transcription factor binding sites, which sequences affect transcription and/or translation of a nucleic acid sequence or gene operably linked to the control sequences.

Presently, the term "operably linked" as used herein, shall mean a functional linkage between a nucleic acid/gene expression control sequence (such as a promoter, signal sequence, or array of transcription factor binding sites) and a second nucleic acid sequence or gene, wherein the expression control sequence affects transcription and/or translation of the nucleic acid corresponding to the second sequence. Accordingly, the term "promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

As outlined already further above, the nucleic acid sequence/gene which is used according to the invention, may, e.g., be comprised in a vector which is to be stably transformed/transfected into bacterial host cells. The definitions and detailed description for recombinant production as outlined above shall apply for this paragraph.

In some embodiments, the nucleic acid sequence/gene is placed under the control of an inducible promoter, which is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the proteins used in the present invention. For *E. coli*—and other bacterial host cells, inducible promoters are known to those of skill in the art.

Throughout the invention, the expression "gene" is meant to represent a linear sequence of nucleotides (or a nucleic acid sequence; see above) along a segment of DNA that provides the coded instructions for synthesis of RNA, which, when translated into protein, leads to the expression of a protein/peptide. The protein/peptide may—as in the present invention—have certain enzymatic functions. A "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

The term "nucleic acid sequence encoding . . . " or "gene(s) encoding/coding for . . . " generally refers to any polyribonucleotide or polydeoxyribonucleotide, which may be unmodified RNA or DNA or modified RNA or DNA, and generally represents a gene which encodes a certain polypeptide or protein. The term includes, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

Accordingly, in the present invention, the terms "gene" and "nucleic acid sequence" are used interchangeably.

Further, as used herein term "activity" when referring to an enzyme is meant to comprise any molecule displaying enzymatic activity, in particular a protein, and acting as a catalyst to bring about a specific biochemical reaction while remaining unchanged by the reaction. In particular, proteins with enzymatic activities are meant to be comprised by this term, which are able to convert a substrate into a product.

In enzymatic reactions, the molecules at the beginning of the process, called substrates, are converted into different molecules, called products. Almost all chemical reactions in a biological cell need enzymes in order to occur at rates sufficient for life. Since enzymes are selective for their substrates and speed up only a few reactions from among many possibilities, the set of enzymes made in a cell determines which metabolic pathways occur in that cell.

Accordingly, when, according to the invention, the activity of an enzyme is "abolished" or "lowered" the enzyme does not have the activity it has if the enzyme or its expression is unmodified, i.e. the activity, in that case, is abolished or lowered compared to the unmodified enzyme/enzyme expression.

The inventors of the present invention were able to provide for a method and a genetically modified host cell, by means of which fucosylated oligosaccharides could be produced with a product titer exceeding 100 g/L.

According to one embodiment of the invention of the method or the host cell of the invention, the activity of a fructose-6-phosphate-converting enzyme, which in the unmodified host cell is—where applicable—at a regular level, is lowered or abolished. When using E. coli as a host cell, it is preferred in the method and the host cell according to the invention the fructose-6-phosphate converting enzyme is selected from the group consisting of phosphofructokinase, preferably phosphofructokinase A (PfKA), glucose-6-phosphate isomerase, fructose-6-phosphate aldolase, a transketolase, preferably tktA, tktB, or a transaldolase, preferably talA, talB, which fructose-6-phosphate converting enzyme, being otherwise present and active in the unmodified E. coli host cell, has been modified such that its activity is lowered or abolished.

PfkA is efficiently phosphorylating fructose-6-phophate to fructose-1,6-bisphosphate. Fructose-6-phosphate is the branching point in glycolytic, and gluconeogenic pathways, and in the synthesis of GDP-L-fucose that starts from the ManA catalyzed isomerization of fructose-6-phosphate to mannose-6-phosphate. When growing E. coli on a gluconeogenic substrate like glycerol, the phosphorylation of fructose-6-phosphate by PfkA is a highly ATP consuming treadmill reaction and, in addition, it competes with ManA for the substrate.

According to an embodiment of the method and the host cell of the invention, the fructose-6-phosphate generating enzyme is fructose-1,6-bisphosphate phosphatase, the activity of which can be increased to increase the pool of fructose-6-phosphate.

According to another embodiment of the invention, at least one gene encoding an enzyme necessary for the de novo synthesis of GDP-fucose is overexpressed in the host cell.

GDP-fucose, as mentioned above, serves as L-fucose-donor for the reaction of the fucosyltransferase transferring L-fucose to an acceptor substrate to form the fucosylated oligosaccharide.

With the prokaryotic host cell genetically modified to internally produce GDP-fucose, an external addition of L-fucose, which can be converted to GDP-fucose via the salvage pathway, is not needed, since the host cell effectively produces GDP-fucose needed for the fucosylation-process of the desired oligosaccharide.

The at least one gene one encoding an enzyme necessary for the de novo synthesis of GDP-fucose and being overexpressed in the host cell can be an endogenous gene or an exogenous gene, which can be integrated into the genome of the host cell.

In an embodiment of the present invention, the exogenous genes encoding the enzymes necessary for the de novo synthesis of GDP-fucose are a gene coding for a phosphomannomutase, preferably manB, a gene coding for amannose-1-phosphate guanosyltransferase, preferably manC, a gene coding for a GDP-mannose-4,6-dehydratase, preferably gmd, and a gene coding for a GDP-L-fucose synthase, preferably wcaG.

According to an embodiment of the invention, and as mentioned further above, at least one exogenous gene encoding a fucosyltransferase is selected from a gene expressing a protein that exhibits an alpha-1,2-fucosyltransferase activity and/or an alpha-1,3-fucosyltransferase activity. In this connection it is particularly preferred if the alpha-1,2-fucosyltransferase is selected from the group consisting of wbgL of *E. coli*:O126 or the alpha-1,2-fucosyltransferase encoded by the fucT 2 gene of *Helicobacter pylori*, and if the gene encoding an alpha-1,3-fucosyltransferase is selected from the group consisting of alpha-1,3-fucosyltransferases of the species *Akkermansia muciniphila* and *Bacteroides fragilis, Helicobacter pylori* or *Helicobacter hepaticus*.

According to another embodiment of the invention it is preferred if the host cell is further genetically modified: (i) to express an gene, preferably an exogenous gene, encoding a protein enabling or facilitating the export of the desired fucosylated oligosaccharide into the culture medium; and/or (ii) to express an exogenous gene encoding a bifunctional L-fucokinase/L-fucose 1-phosphate guanylyltransferase; and/or (iii) to exhibit mutated or deleted genes fucI and fucK leading to lowered or abolished activities of the L-fucoseisomerase (FucI) and L-fuculose-kinase (fucK), (iv) and/or to have inactivated or disrupted genes encoding enzymes of the colonic acid synthesis; and/or (v) to express, preferably overexpress, an endogenous and/or exogenous permease for the import of lactose; and/or (vi) to have inactivated or deleted endogenous beta-galactosidase genes; and/or (vii) to express a gene encoding beta-galactosidase, preferably an exogenous regulable beta-galactosidase; and/or (viii) to overexpress an endogenous and/or exogenous gene coding for a fructose-1,6-bisphosphate phosphatase.

With the additional genetic modification as indicated above, the method for producing a fucosylated oligosaccharide could be even more improved.

With the deletion or inactivation of the genes encoding L-fucose isomerase (e.g., FucI) and L-fuculose-kinase (e.g., fucK), the catabolism of intracellular fucose can be avoided.

With the disruption, deletion or inactivation of genes encoding enzymes of the colonic acid biosynthesis (e.g., in E. coli as host cell, the wcaJ gene that catalyzes the first step of colonic acid synthesis), the intracellularly production of colonic acid, which otherwise might compete with the fucosyltransferase reaction for the substrate GDP-L-fucose, is prevented.

According to a preferred embodiment, the protein that enables or facilitates the export of the desired fucosylated oligosaccharide into the culture medium is a sugar efflux transporter preferably selected from yberc0001_9420 and E. coli SetA.

According to a preferred embodiment, the gene encoding a bifunctional L-fucokinase/L-fucose 1-phosphate guanylyltransferase is fkp from Bacteroides fragilis.

According to a preferred embodiment, the fructose-1,6-bisphosphate phosphatase is encoded by a gene which is a functional active variant of the fructose-1,6-bisphosphate phosphatase (fbpase) from Pisum sativum.

According to a preferred embodiment, the lactose permease is E. coli LacY.

With the expression of a gene encoding a bifunctional L-fucokinase/L-fucose 1-phosphate guanylyltransferase that catalyzes the synthesis of GDP-L-fucose, e.g. of the Bacteroides fragilis fkp gene, the formation of free L-fucose that could accumulate as a byproduct following the hydrolysis of GDP-L-fucose is prevented, thereby rescuing free L-fucose for the synthesis of the desired fucosylated oligosaccharide.

According to a preferred embodiment, the exogenous genes for metabolizing galactose are the genes comprising the galETKM operon and/or galP from E. coli.

According to an embodiment of the invention, the genes the host cell is modified in or with are endogenous or exogenous genes.

Throughout the invention, and applying for each gene/nucleic acid that has been exogenously introduced into the host cell, it is—according to an embodiment of the present method and host cell—preferred, if at least one of the exogenous genes, preferably integrated in the host cell genome, is overexpressed, preferably upon endogenous or exogenous induction, or in a constitutive manner.

Accordingly, it is preferred if at least one of the following gene(s) is/are overexpressed: (i) exogenous genes encoding enzymes necessary for the de novo synthesis of GDP-fucose; (ii) an exogenous gene encoding a fucosyltransferase; (iii) an exogenous gene encoding a sugar efflux transporter; (iv) an exogenous gene encoding a bifunctional L-fucokinase/L-fucose 1-phosphate guanylyltransferase; (v) a lactose permease; (vi) an exogenous regulable gene encoding a beta-galactosidase; and/or (vii) exogenous genes for metabolizing galactose; (viii) an exogeneous gene encoding a fructose-1,6-bisphospahate phosphatase; the overexpression can be effected, e.g., by means of a regulable promoter that initiates transcription of the gene(s), either at a certain time point or period during the cultivation or for the whole cultivation time.

Also, according to a preferred embodiment, the exogenous genes to be introduced in the host cell employed in the method according to the invention are integrated into the genome of the host cell.

Also, according to one aspect of the invention, and unless otherwise defined, the genes the host cell is modified in/with according to the invention can also be endogenous genes, and their expression can be enhanced or increased or overexpressed, or otherwise abolished or decreased.

With the inactivation or deletion of endogenous beta-galactosidase gene(s) the degradation of externally added lactose is prevented; however, since it is desirable to have lactose degraded that is not metabolized and that would otherwise impede the purification of the desired fucosylated oligosaccharide, it is also preferred if an exogenous regulable gene encoding a beta-galactosidase or a mutated form of the beta-galactosidase is expressed in the host cell. E.g., the lacZΩ fragment of the lacZ gene can be expressed, the expression of which, e.g., can be regulated by means of a repressor, e.g. by a temperature sensitive transcriptional repressor, e.g. cI857. In this case, synthesis of the beta-galactosidase Ω-fragment can be initiated by raising the temperature to 42° C.

A repressor, as presently and generally in the state of the art understood, is a DNA- or RNA-binding protein that inhibits the expression of one or more genes by binding to the operator or associated silencers. A DNA-binding repressor blocks the attachment of RNA polymerase to the promoter, thus preventing transcription of the genes into messenger RNA.

As a promoter for the exogenous beta-galactosidase alpha fragment, e.g., the E. coli BL21 (DE3) PgbA promoter can be used. The beta-galactosidase α- and Ω-fragments are combined to result in an active beta-galactosidase in the cell.

In a preferred embodiment, the lactose is provided by adding lactose from the beginning of the cultivation in a concentration of at least 5 mM, more preferably in a concentration of more than 10, 20, 30, 40, 50, 60, 70, 80, 90 or 100 mM, or even more in a concentration of 300 mM or higher than 300, or 400 mM.

According to yet another embodiment, lactose is provided by adding lactose the cultivation medium in a concentration, such, that throughout the production phase of the cultivation a lactose concentration of at least 5 mM, more preferably of at least 10, 20 or 30 mM, is obtained.

Alternatively, lactose can be produced by the host cell intracellularly, as described in patent EP1927316 A1, the content of which is herewith expressively referred to and incorporated by reference.

In the method according to the invention, it is preferred if the host cells are cultivated for at least about 60, 80, 100 or about 120 hours or in a continuous manner.

Thus, according to one aspect of the invention, i.e. in a continuous method, a carbon source is constantly added to the medium during the cultivating step of the host cell. By constantly adding the carbon source during the cultivation step, a constant and effective production of the oligosaccharide is accomplished.

According to another aspect, the method according to the invention is or includes a fed-batch fermentation method, with either a constant volume fed-batch culture, where the substrate is fed without diluting the culture, or variable volume fed-batch culture, where the fermentation volume changes with the fermentation time due to the substrate feed.

As mentioned above, the present invention also concerns a genetically modified prokaryotic host cell, which host cell has been genetically modified such, that (i) the activity of a fructose-6-phosphate-converting enzyme, which in the unmodified host cell is at a regular level, is lowered or abolished; (ii) at least one gene encoding an enzyme necessary for the de novo synthesis of GDP-fucose is overexpressed; (iii) an exogenous gene encoding a fucosyltransferase, preferably a gene encoding an alpha-1,2-fucosyltransferase and/or an alpha-1,3-fucosyltranferase, is expressed in the cell.

As mentioned for the method above, the host cell is preferably selected from a *Escherichia coli* strain, a *Lactobacillus* strain or a *Corynebacterium* strain.

According to an embodiment of the host cell according to the invention, the intracellular pool of fructose-6-phosphate is increased by (i) lowering or abolishing the activity of a fructose-6-phosphate converting enzyme that is selected from the group of phosphofructokinase, glucose-6-phosphate isomerase, fructose-6-phosphate aldolase, a transketolase, e.g. tktA, tktB, or a transaldolase, e.g. talA, talB, or (ii) increasing the fructose-1,6-bisphosphate phosphatase activity.

In a preferred embodiment, the genes encoding enzymes necessary for the de novo synthesis of GDP-fucose are overexpressed.

In yet another preferred embodiment, the exogenous genes encoding at least one fucosyltransferase are genes encoding alpha-1,2-fucosylltransferases and/or alpha-1,3-fucosyltransferases and are selected from wbgL from *E. coli* O126 or fucT2 from *Helicobacter pylori*, referring to alpha-1,2-fucosylltransferases, and genes of the species *Akkermansia muciniphila, Bacteroides fragilis, Helicobacter pylori*, or *Helicobacter hepaticus*, referring to alpha-1,3-fucosyltransferases.

According to an embodiment, the host cell as described above is optionally genetically further modified (iv) to express an exogenous gene encoding a sugar efflux transporter; and/or (v) to express an exogenous gene encoding a bifunctional L-fucokinase/L-fucose 1-phosphate guanylyltransferase; and/or (vi) to have inactivated or deleted genes encoding a L-fucose-isomerase and L-fuculose-kinase; and/or (vii) to have inactivated or disrupted genes encoding the UDP-glucose:undecaprenyl phosphate glucose-1-phosphate transferase; and/or (viii) to express an exogenous lactose permease; and/or (ix) to have inactivated or deleted endogenous beta-galactosidase genes; and/or (x) to express an exogenous regulable gene encoding a beta-galactosidase; and/or (xi) to express exogenous genes for metabolizing galactose; and/or to express an exogenous gene encoding a fructose-1,6-bisphosphare phosphatase.

The present invention also concerns the use of the genetically modified prokaryotic host cell according to the invention for the production of a fucosylated oligosaccharide Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

BRIEF DESCRIPTION OF THE FIGURES

Several embodiments of the invention are illustrated in the figures and explained in more detail in the following description. In the figures:

FIG. 3 SEQ ID NOs: 1-7.

DETAILED DESCRIPTION OF THE FIGURES AND EMBODIMENTS

Figure 1:
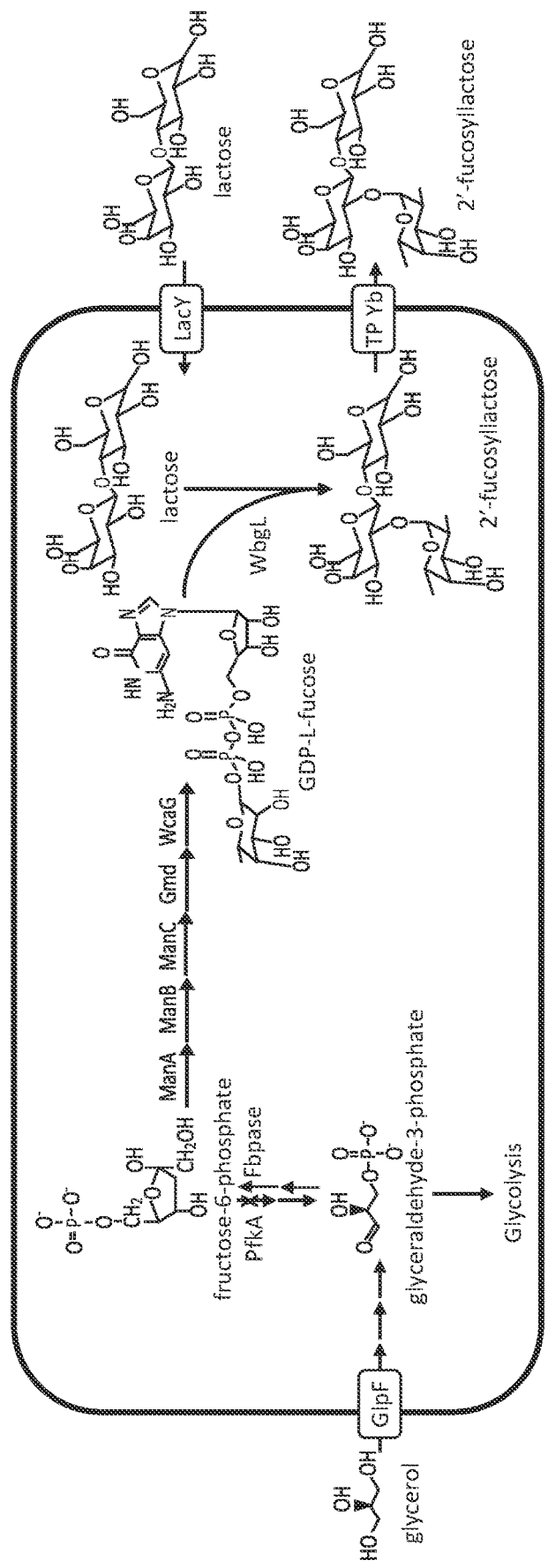
FIG. 1 A schematic, exemplary illustration of a genetically modified host cell to be used in the method according to the invention.

FIG. 1 shows an exemplary illustrative host cell according to the invention to be employed in the method according to the invention, with exemplary pathways for the fermentation of the exemplary fucosylated oligosaccharides 2'-fucosyllactose being depicted. In FIG. 1, an exemplary bacterial host cell is shown that has been genetically modified according to the invention, with respect to the production of 2'-fucosyllactose.

As can be seen from FIG. 1, glycerol is exemplary used as carbon source, while lactose is externally added. Lactose is transported into the host cell via a permease (e.g. LacY). Glycerol is taken up into the host cell via facilitated diffusion through GlpF. Within the prokaryotic host cell, glycerol is converted into glyceraldehyde-3-phosphate, which is converted to fructose-6-phosphate, (i) favored by the overexpression of an exogenous gene encoding a Fbpase and (ii) with the reverse reaction being inhibited by the inactivation of the phosphofructokinase A (PfkA). Via overexpression of exogenous enzymes necessary for the de novo synthesis of GDP-fucose, i.e. phosphomannomutase ManB, mannose-1-phosphate guanosyltransferase ManC, GDP-mannose-4,6-dehydratase Gmd, and GDP-L-fucose synthase WcaG, GDP-L-fucose is produced.

In a next step, GDP-L-fucose, by the action of an alpha-1,2-fucosyltransferase, e.g. WbgL, reacts with the internalized lactose to produce 2-fucosyllactose, which is exported via an efflux transporter, e.g. TPYb, into the medium the host cell is cultivated in.

Figure 2:
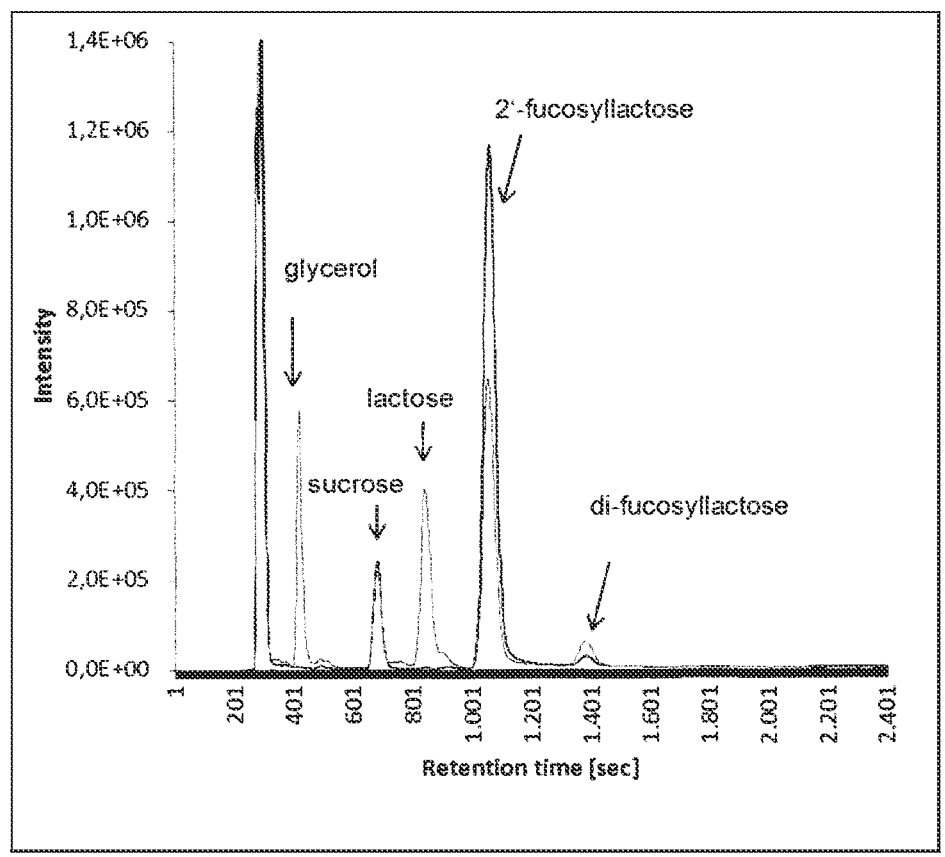
FIG. 2 HPLC analyses of supernatants from glycerol grown cultures of 2'-fucosyllactose producing *E. coli* strains by HPLC.

In FIG. 2 the results of HPLC analyses of supernatants from glycerol grown cultures of 2'-fucosyllactose producing *E. coli* strains by HPLC are shown.

Depicted in FIG. 2 is the HPLC profile of the fermentation broth from a 2'-fucosyllactose producing strain harbouring the gene encoding the heterologous transporter yberc0001_9420 (black) and the HPLC profile of fermentation broth of the same strain after deletion of the gene encoding the heterologous transporter yberc0001_9420 (gray). Fermentation of both strains was conducted for 111 h at 28° C., using glycerol as source of carbon and energy.

Example 1

Engineering of an *E. coli* BL21(DE3) Strain for the Production of 2'-Fucosyllactose Using *E. coli* BL21(DE3) as parental host a strain for the production of 2'-fucosyllactose in a whole cell biosynthetic approach was constructed. Genomic engineering of the strain included gene disruption and deletion events and integration of heterologous genes.

Since 2'-fucosyllactose is synthesized from lactose, that is applied to the bacterial culture, and from GDP-L-fucose that is produced from the living cells, first the wild-type copy of the lacZgene encoding the endogenous (3-galactosidase was inactivated by mutagenesis using mismatch oligonucleotides (see Ellis et al., "High efficiency mutagenesis, repair, and engineering of chromosomal DNA using single-stranded oligonucleotides", Proc. Natl. Acad. Sci. USA 98: 6742-6746 (2001). Using the same method, the gene for the arabinose-isomerase araA was disrupted.

A lacZΩ gene fragment was introduced under the control of the temperature sensitive transcriptional repressor cI857. The lacZα fragment gene is expressed under the control of the E. coli BL21 (DE3) PgbA promoter in the strain, revealing a LacZ+ strain.

Genomic deletions were performed by λ Red mediated recombination according to the method of Datsenko and Warner (see "One-step inactivation of chromosomal genes in Escherichia coli K-12 using PCR products", Proc. Natl. Acad. Sci. USA 97:6640-6645 (2000)). The genes fucI and fucK, coding for the L-fucose isomerase and the L-fuculose kinase, respectively, have been deleted to prevent degradation of L-fucose. Also genes wzxC-wcaJ were deleted. WcaJ probably encodes a UDP-glucose:undecaprenyl phosphate glucose-1-phosphate transferase catalysing the first step in colanic acid synthesis (see Stevenson et al., "Organization of the Escherichia coli K-12 gene cluster responsible for production of the extracellular polysaccharide colonic acid", J. Bacteriol. 178:4885-4893; (1996)); production of colanic acid would compete for GDP-fucose with the fucosyltransferase reaction.

Genomic integration of heterologous genes was performed by transposition. Large gene clusters were integrated into the genome mediated by the hyperactive C9-mutant of the mariner transposase Himar1 (see Lampe et al., "Hyperactive transposase mutants of the Himar1 mariner transposon", Proc. Natl. Acad. Sci. USA 96:11428-11433 (1999)), that was inserted into the plasmid pEcomar under transcriptional control of the $P_{ara}$ promoter. To enhance de novo synthesis of GDP-fucose, genes encoding phosphomannomutase (manB), mannose-1-phosphate guanosyltransferase (manC), GDP-mannose-4,6-dehydratase (gmd), and GDP-L-fucose synthase (wcaG) from E. coli K12 DH5α were overexpressed in the E. coli BL21(DE3) strain; the operon manCB was set under control of the constitutive promoter $P_{tet}$, the operon gmd, wcaG is transcribed from the constitutive $P_{T5}$ promoter. The transposon cassette <$P_{tet}$-manCB-$P_{T5}$-gmd, wcaG-FRT-dhfr-FRT> (SEQ ID No. 1), including the gene for the dihydrofolate reductase for trimethoprim resistance, flanked by the inverted terminal repeats specifically recognized by the mariner-like element Himar1 transposase was inserted into the E. coli genome from pEcomar C9-manCB-gmd, wcaG-dhfr.

For chromosomal integration of single genes, the EZ-Tn5™ transposase (Epicentre, USA) was used. To produce EZ-Tn5 transposomes the gene of interest together with a FRT-site flanked antibiotic resistance cassette was amplified with primers that carried on both sites the 19-bp Mosaic End recognition sites (5'-CTGTCTCTTATAC ACATCT (SEQ ID No. 8)) for the EZ-Tn5 transposase. Using the EZ-Tn5™ transposase, the gene for the lactose importer LacY from E. coli K12 TG1 (acc. no. ABN72583), the 2-fucosyltransferase gene wbgL from E. coli:O126 (acc. no. ADN43847), and the gene yberc0001_9420 encoding a sugar efflux transporter of the major facilitator superfamily from Yersinia bercovieri ATCC 43970 (acc. no. EEQ08298) were integrated using the respective integration cassettes: <$P_{tet}$-lacY-FRT-aadA-FRT> (SEQ ID No. 2), <$P_{tet}$-wbgLco-FRT-neo-FRT> (SEQ ID No. 3), and <$P_{tet}$-yberc0001_9420co-FRT-cat-FRT> (SEQ ID No. 4), yielding strain. The genes wbgL and yberc0001_9420 were synthetically synthesized and codon optimized (co) by GenScript Cooperation (USA). After successful integration of the lacY gene the resistance gene was eliminated from streptomycin resistant clones by the FLP recombinase encoded on plasmid pCP20 (Datsenko and Warner, "One-step inactivation of chromosomal genes in Escherichia coli K-12 using PCR products", Proc. Natl. Acad. Sci. USA 97:6640-6645 (2000)).

Since E. coli BL21(DE3) lacks a functional gal-operon a natively regulated copy of the galETKM operon from E. coli K was integrated into the B strain by EZ-transposition using integration cassette <$P_{gal}$-galE-galT-galK-galM> (SEQ ID No. 5). Integrands were selected from MacConkey-agar containing 1% galactose as red colonies. The resulting strain is able to metabolize the monosaccharides glucose and galactose originating from lactose hydrolysis.

Example 2

Verification of Enhanced 2'-Fucosyllactose Export by Yersinia bercovieri ATCC 43970 Sugar Efflux Transporter Knock-Out of yberc0001_9420

To demonstrate functionality of the heterologous sugar transporter from Yersinia bercovieri ATCC 43970 the gene yberc0001_9420 was deleted from strain strain E. coli BL21(DE3) lacZ-, araA-, fucI-, fucK-, wcaJ-, that contained chromosomal integrations of manB, manC, gmd, wcaG, lacY, wbgL; and yberc0001_9420 by homologous recombination according to Datsenko and Wanner (2000; see above) using the gentamycine resistance cassette aacC1 from plasmid pBBR-MCS5 (Kovach, Elzer et al. 1995, "Four new derivatives of the broad-host-range cloning vector pBBR1 MCS, carrying different antibiotic-resistance cassettes", Gene 166, 175-176), that was inserted into gene yberc0001_9420, yielding strain Δyberc0001_9420.

Cultivation Conditions for 2'-Fucosyllactose Production

The E. coli BL21 (DE3) strain harbouring the heterologous exporter yberc0001_9420 and the Δyberc0001_9420 strain were cultivated at 28° C. in 3 L fermenters (New Brunswick, Edison, USA) starting with 800 mL mineral salts medium containing 7 g/L $NH_4H_2PO_4$, 7 g/L $K_2HPO_4$, 2 g/L KOH, 0.3 g/L citric acid, 2 g/L $MgSO_4 \times 7H_2O$, and 0.015 g/L $CaCl_2 \times 6H_2O$, supplemented with 1 mL/L trace element solution (54.4 g/L ammonium ferric citrate, 9.8 g/L $MnCl_2 \times 4H_2O$, 1.6 g/L $CoCl_2 \times 6H_2O$, 1 g/L $CuCl_2 \times 2H_2O$, 1.9 g/L $H_3BO_3$, 9 g/L $ZnSO_4 \times 7H_2O$, 1.1 g/L $Na_2MoO_4 \times 2H_2O$, 1.5 g/L $Na_2SeO_3$, 1.5 g/L $NiSO_4 \times 6H_2O$) containing 1.5% glycerol as carbon source and the antibiotics trimethoprim 10 μg/ml, and kanamycin 15 μg/ml. Cultivation was started with a 2.5% (v/v) inoculum from a pre-culture grown in the same glycerol containing medium. Lactose as acceptor in the fucosyltransferase reaction was added within seven hours to obtain a concentration of 30 mM in the culture, starting at $OD660_{nm}$ of about 10. Lactose was then adjusted manually to maintain an excess of the acceptor molecule; glycerol was added continuously.

Analysis of Culture Supernatant and Detection of 2'-Fucosyllactose by HPLC

Analysis by high performance liquid chromatography (HPLC) was performed using a refractive index detector (RID-10A) (Shimadzu, Germany) and a ReproSil Carbohydrate, 5 μm (250 mm×4.6 mm) (Dr. Maisch GmbH, Germany) connected to an HPLC system (Shimadzu, Germany). Elution was performed isocratically with acetonitril:$H_2O$ (68/32 (v/v)) as eluent at 35° C. and a flow rate of 1.4 ml/min. 20 μl of the sample were applied to the column. 2'-fucosyllactoseconcentration was calculated from a standard curve. Therefore, 10% (v/v) 100 mM sucrose were added to the HPLC samples as internal standard before they were filtered (0.22 μm pore size) and cleared by solid phase extraction on an ion exchange matrix (Strata ABW, Phenomenex).

Detection of 2'-Fucosyllactose in Supernatants of *E. coli* BL21(DE3) Cultures

After 111 h of fermentation at 28° C. in mineral salts medium with glycerol as carbon source, 73 mM (35.6 g/L) and 25 mM (12.2 g/L) 2'-fucosyllactose were detected by HPLC in the culture supernatant of strains containing, and lacking the yberc0001_9420 transporter gene, see FIG. 2: Depicted in FIG. 2 is the HPLC profile of the fermentation broth from a 2'-fucosyllactose producing strain harbouring the gene encoding the heterologous transporter yberc0001_9420 (black) and the HPLC profile of fermentation broth of the same strain after deletion of the gene encoding the heterologous transporter yberc0001_9420 (gray). Deletion of the heterologous sugar exporter yberc0001_9420 in the strain decreases the detected amount of 2'-fucosyllactose in the supernatant. That gives evidence, that indeed the transporter protein enhances 2'-fucosyllactose production by faster transport of the tri-saccharide outside the cell, since the genetic background despite the yberc0001_9420 gene is identical in both strains. Additionally, a lower cell density was achieved in the cells lacking the 2'-fucosyllactose exporter, probably due to osmotic stress caused by strong sugar accumulation inside the cells. As shown in FIG. 2, the amount of 2',3-difucosyllactose detected in the Δyberc0001_9420 culture is about double than in the broth of the original strain. Increased production of 2',3-difucosyllactose, where L-fucose is transferred to 2'-fucosyllactose by a fucosyltransferase catalyzed reaction, also suggests higher intracellular concentrations of the acceptor molecule 2'-fucosyllactose in the yberc0001_9420 knock-out strain as compared to the yberc0001_9420 overexpression strain.

In FIG. 2, the lighter lines, i.e. the grey lines, display the supernatant of the Δyberc0001_9420 *E. coli* BL21(DE3) strain Δyberc0001_9420, the black lines display the supernatant of the culture of the yberc0001_9420 containing *E. coli* BL21(DE3). Samples were taken after 111 h of fermentation at 28° C. in mineral salts medium using glycerol as carbon source.

Example 3

Production of 2'-fucosyllactose in a Fermentative Process

Fermentations were conducted in 3 L-fermenters at 30 CC and at pH 7.0; the pH was regulated by titration with 25% ammonia. The strain described in example 2 was cultivated in the mineral salts medium described in example 2 using glycerol as source of carbon and energy. The fermenter with a starting volume of 1 L was inoculated with a pre-culture cultivated in the same medium. After consumption of the 2% glycerol contained within the batch, glycerol (60% v/v) was fed continuously. Lactose in a concentration of 0.66 M was added in three portions (in an one hour interval) of 10 mL each when an $OD_{600nm}$ of 6 was reached. Afterwards, lactose was given in a continuous flow to hold a lactose concentration of at least 10 mM in the fermenter. After 86 h of cultivation a final titer of 91.3 mM (44.6 g/L) 2'-fucosyllactose was reached. By shifting the temperature to 42° C., the β-galactosidase gene is expressed and lactose and its degradation products glucose and galactose are metabolized by the 2'-fucosyllactose production strain.

Example 4

HPLC-Analysis of Culture Supernatant

Analysis by HPLC was performed using a refractive index detector (RID-10A) (Shimadzu, Germany) and a Waters XBridge Amide Column 3.5 μm (250×4.6 mm) (Eschborn, Germany) connected to an HPLC system (Shimadzu, Germany). Elution was performed isocratically with 30% A: 50% (v/v) ACN in $ddH_2O$, 0.1% (v/v) $NH_4OH$ and 70% B: 80% (v/v) ACN in $ddH_2O$, 0.1% (v/v) $NH_4OH$ (v/v) as eluent at 35° C. and at a flow rate of 1.4 ml/min. 10 μl of the sample were applied to the column, and the 2'-fucosyllactose concentration was calculated from a standard curve. Therefore, 10% (v/v) of a 100 mM sucrose solution was added to the HPLC samples as an internal standard prior to filtering (0.22 μm pore size) and clearing by solid phase extraction on an ion exchange matrix (Strata ABW, Phenomenex). By-products like L-fucose, 3-fucosyllactose, 2',3-difucosyllactose, and fucosylgalactose were also detected using the same analysis conditions.

Example 5

Improvement of 2'-Fucosyllactose Production Strain by Metabolic Engineering

Further improvement concerning the synthesis of 2'-fucosyllactose by the *E. coli* strain was achieved by deletion of the pfkA gene, encoding the phosphofructokinase A. When cultivating *E. coli* on a gluconeogenic substrate like glycerol the phosphorylation of fructose-6-phosphate by PfkA is a highly ATP consuming treadmill reaction and, in addition, it competes with ManA for the substrate. The pfkA gene was deleted by homologous recombination according to Datsenko and Wanner (2000, see above) using a gentamycin resistance cassette (aacC1) that was flanked by lox71/66 sites (see Lambert, Bongers et al. 2007 "Cre-lox-based system for multiple gene deletions and selectable-marker removal in *Lactobacillus plantarum*", Appl. Environ. Microbial. 73, 1126-113). After successful deletion the pfkA gene the antibiotic resistance gene was removed from *E. coli* genome using the Cre recombinase (see Abremski, Hoess et al. 1983, "Studies on the properties of P1 site-specific recombination: evidence for topologically unlinked products following recombination", Cell 32, 1301-1311) that was cloned under the control of the $P_{ara}$ promoter in the pKD46 (see Datsenko and Wanner, 2000) chassis.

For different fucosyltransferases besides the transferase activity a GDP-L-fucose hydrolase activity was demonstrated. Also for wbgL, the alpha-1,2-fucosyltransferase used here for 2'-fucosyllactose synthesis this hydrolytic activity was shown (see EP3050973 A1). To rescue free L-fucose for the 2'-fucosyllactose production and to eliminate the contaminating L-fucose from the culture broth, the fkp gene, encoding the bifunctional L-fucokinase/L-fucose 1-phosphat guanylyltranferase of *Bacteroides fragilis*, under transcriptional control of the $P_{tet}$ promoter, together with the lox71/66 flanked aacC1 gene was chromosomally integrated into the strain described in example 1 by transposition using the EZ-Tn5™ transposase, <Ptet-fkp-lox-aacC1-lox> (Seq ID 6). After successful integration the gentamycin resistance gene was removed from the genome as described above.

Example 6

Optimized Fermentation Process for the Production of 2'-Fucosyllactose

Using an optimized mineral salts medium that contains 3 g/L $KH_2PO_4$, 12 g/L $K_2HPO_4$, 5 g/L $(NH_4)_2SO_4$, 0.3 g/L citric acid, 2 g/L $MgSO_4 \times 7H_2O$, 0.1 g/L NaCl and 0.015 g/L $CaCl_2 \times 6H_2O$ with 1 mL/L trace element solution (54.4 g/L ammonium ferric citrate, 9.8 g/L $MnCl_2 \times 4H_2O$, 1.6 g/L $CoCl_2 \times 6H_2O$, 1 g/L $CuCl_2 \times 2H_2O$, 1.9 g/L $H_3BO_3$, 9 g/L $ZnSO_4 \times 7H_2O$, 1.1 g/L $Na_2MoO_4 \times 2H_2O$, 1.5 g/L $Na_2SeO_3$, 1.5 g/L $NiSO_4 \times 6H_2O$) and 2% glycerol as carbon source batch, the E. coli strain described in example 5 was cultivated in a 3 L fermenter at 33° C. The pH was hold at 7.0 by titrating 25% ammonia. The fermenter was inoculated to an $OD_{600nm}$ of 0.1 with a pre-culture grown in the same medium. Lactose was added when the culture obtained an $OD_{600nm}$ of 5, to obtain a concentration of 30 mM. A concentration of 20-30 mM lactose was held throughout the whole fermentation process, regulated according to HPLC-analyses. Glycerol feeding (60% v/v) started after the glycerol in the batch was consumed with flow rates of 4.5 ml/L/h for 20 hours, followed by feeding for 33 hours with 5.7 ml/L/h and 18 hours for 7.1 ml/L/h over a period of 18 hours (feeding rates are referring to the starting volume). Overall, after 93 h a 2'-fucosyllactose titer of 106.5 g/L (217 mM) was obtained.

Example 7

Engineering of an Enhanced 2'-fucosyllactose Production Strain by Metabolic Challenging To enhance the flux of the metabolized carbon source glycerol through the gluconeogentic pathway from triose-phosphates to fructose-6-phophate to feed the GDP-L-fucose biosynthesis the genes encoding the fructose-1,6-bisphosphate aldolase (fbaB) and a heterologous fructose-1,6-bisphosphate phosphatase (fbpase) from Pisum sativum were overexpressed in the strain described in example 5. The fbaB gene from E. coli BL21 (DE3) was fused with the Ptet promoter. The activity of the chloroplasic P. sativum FBPase is allosterically regulated by a disulfide-dithiol exchange due to reduction by thioredoxins. Exchange of the cysteine residue 153 to serine results in a constitutively active enzyme. The gene encoding the chloroplastic FBPase from P. sativum (acc. No. AAD10213) was purchased codon optimized for expression in E. coli, N-terminally tagged with a hexahistidine-tag and modified to encode the C153S variant of the enzyme from Genescript. The fbpase gene is transcribed from a T7 promoter. The cassette <$P_{tet}$-fbaB-$P_{T7}$-$His_6$-fbpase-lox-aacC1-lox> (Seq ID 7) was used for EZ-Tn5™ transposase mediated integration in the host strain. After removal of the gentamycin resistance gene from the E. coli genome the strain was used for 2'-fucosyllactose production.

Example 8

Production of 150 g/L 2'-Fucosyllactose by a Fermentation Process

The 2'-fucosyllactose production strain genetically modified as described in example 7 was cultivated in the same medium at 33° C. as described in example 5. Additionally, to the 2% glycerol batch 60 mM lactose were added initially to the fermentation medium. Continuous lactose feeding with 0.66 M lactose was stared at an $OD_{600\ nm}$ of about 10. Additionally, lactose supplementation was carried out with a 1 M stock-solution. The lactose concentration was kept at approximately at 30 mM. After leaving the batch phase, indicated by a rise in the dissolved oxygen level, the glycerol feed (60% v/v) started with a flow rate of 6.9 ml/L/h for 37 hours (referring to the starting volume). Afterwards the feed was reduced to 9.4 ml/L/h for 19 hours, and then raised again to 7.3 ml/L/h for 19 hours. 93 hours after seeding the fermenter a 2'-fucosyllactose titer of 150.2 g/L was reached.

Example 9

Production of 3-Fucosyllactose from Glycerol

Using E. coli BL21 (DE3) lacZ ΔwcaJ ΔfucIK with chromosomal integration of the genes encoding the enzymes for de novo synthesis of GDP-Fucose (ManB, ManC, Gmd, WcaG) a 3-fucosyllactose production strain was constructed.

The gene encoding the alpha-1,3-fucosylltransefrase from Bacteroides fragilis (EP 2439264 A1) together with the gene encoding the sugar efflux transporter SetA from E. coli (US2014/0120611 A1) and a gene conferring gentamycin resistance was integrated into the E. coli genome. Fermentation of the strain to produce 3-fucosyllactose was conducted under conditions described in example 6. Glycerol feeding started after leaving the batch phase with a feeding rate of 7.4 ml/L/h (referring to the starting volume). Lactose was added to the culture to a concentration of 33 mM, when an $OD_{600\ nm}$ of 30 was reached. Throughout the process, lactose was added to hold a concentration of at least 10 mM in the supernatant. After 88 h the process was stopped at a 3-fucosyllactose concentration in the supernatant of 30 g/L.

The invention claimed is:

1. A method for the production of fucosylated oligosaccharides using a genetically modified prokaryotic host cell, the method comprising:
   providing a prokaryotic host cell which has been genetically modified to have:
   (i) reduced or abolished activity of a fructose-6-phosphate-converting enzyme as compared to the activity in an unmodified prokaryotic host cell, wherein the fructose-6-phosphate converting enzyme is selected from the group consisting of phosphofructokinase, glucose-6-phosphate isomerase, fructose-6-phosphate aldolase, a transketolase, and a transaldolase;
   (ii) overexpression of at least one gene encoding an enzyme necessary for the de novo synthesis of GDP-fucose, wherein said at least one gene encoding an enzyme necessary for the de novo synthesis of GDP-fucose is a phosphomannomutase encoding gene, a mannose-1-phosphate guanosyltransferase encoding gene, a GDP-mannose-4,6-dehydratase encoding gene, or a GDP-L-fucose synthase encoding gene; and
   (iii) expression of an exogenous gene encoding an alpha-1,2-fucosyltransferase and/or an alpha-1,3-fucosyltransferase; and
   cultivating said genetically modified prokaryotic host cell in a cultivation medium comprising at least one carbon and/or energy source selected from one or more of the group consisting of glycerol, succinate, malate, pyruvate, lactate, ethanol, and citrate; and
   adding lactose to the cultivation medium;
   wherein the fucosylated oligosaccharide is obtained from the medium in which the host cell is cultivated; and
   wherein said genetically modified prokaryotic host cell has an intracellular pool of fructose-6-phosphate that is increased by increasing the activity of a fructose-1,6-bisphosphate phosphatase.

2. The method of claim 1, wherein the fucosylated oligosaccharide is selected from the group consisting of 2'-fucosyllactose, 3-fucosyllactose or difucosyllactose.

3. The method of claim 1, wherein the prokaryotic host cell is selected from the group consisting of bacterial cells from an *Escherichia coli* strain, a *Lactobacillus* species or a *Corynebacterium glutamicum* strain.

4. The method of claim 1, wherein the phosphomannomutase encoding gene is manB, the mannose-1-phosphate guanosyltransferase encoding gene is manC, the GDP-mannose-4,6-dehydratase encoding gene is gmd, and/or the GDP-L-fucose synthase encoding gene is wcaG.

5. The method of claim 1, wherein the gene encoding the alpha-1,2-fucosyltransferase is wbgL from *E. coli* O126 or fucT2 from *Helicobacter pylori*.

6. The method of claim 1, wherein the gene encoding the alpha-1,3-fucosyltransferase is from the species *Akkermansia muciniphila, Bacteroides fragilis, Helicobacter pylori*, or *Helicobacter hepaticus*.

7. The method of claim 1, wherein the host cell is further genetically modified to express a gene encoding a protein which enables or facilitates the export of a fucosylated oligosaccharide into the culture medium.

8. The method of claim 1, wherein the host cell is further genetically modified to overexpress an endogenous or exogenous permease for the import of lactose.

9. The method of claim 1, wherein at least one of the expressed or overexpressed genes in (ii) or (iii) is expressed or overexpressed in a constitutive manner.

10. The method of claim 7, wherein the gene encoding a protein which enables or facilitates the export of the desired fucosylated oligosaccharide is a sugar efflux transporter selected from the group consisting of yberc0001_9420 and setA.

11. The method of claim 1, wherein the fructose-1,6-bisphosphate phosphatase is encoded by a gene which is a functional active variant of the fructose-1,6-bisphosphate phosphatase (fbpase) from *Pisum sativum*.

12. The method of claim 8, wherein the lactose permease is *E. coli* LacY.

13. The method of claim 1, wherein the lactose is added from the beginning of the cultivating in a concentration of at least 5 mM, optionally in a concentration of 30, 40, 50, 60, 70, 80, 90, 100, 150 mM, optionally in a concentration >300 mM.

14. The method of claim 1, wherein providing of lactose is accomplished by adding lactose to the cultivation medium in a concentration, such that throughout the production phase of the cultivation a lactose concentration of at least 5 mM.

15. The method of claim 1, wherein the host cells are cultivated for at least about 60, 80, 100, or about 120 hours or in a continuous manner.

16. The method of claim 1, wherein the modified genes are integrated into the genome of the host strain.

17. The method of claim 14, wherein the lactose concentration is at least 10 mM.

18. The method of claim 14, wherein the lactose concentration is at least 30 mM.

* * * * *

SEQUENCE LISTING

```
<160> NUMBER OF SEQ ID NOS: 8

<210> SEQ ID NO 1
<211> LENGTH: 6783
<212> TYPE: DNA
<213> ORGANISM: Artificial Sequenz
<220> FEATURE:
<223> OTHER INFORMATION: Transposon cassette

<400> SEQUENCE: 1
gccagatgat taattcctaa ttttgttga cactctatca ttgatagagt tattttacca    60
```

-continued

```
ctccctatca gtgatagaga aaagtgaaat gaatagttcg acaaaaatct agaaataatt    120
ttgtttaact ttaagaagga gatatacaat ttcgtcgaca cacaggaaac atattaaaaa    180
ttaaaacctg caggagtttg aaggagatag aaccatggcg cagtcgaaac tctatccagt    240
tgtgatggca ggtggctccg gtagccgctt atggccgctt tcccgcgtac tttatcccaa    300
gcagttttta tgcctgaaag gcgatctcac catgctgcaa accaccatct gccgcctgaa    360
cggcgtggag tgcgaaagcc cggtggtgat ttgcaatgag cagcaccgct ttattgtcgc    420
ggaacagctg cgtcaactga acaaacttac cgagaacatt attctcgaac cggcagggcg    480
aaacacggca cctgccattg cgctggcggc gctggcggca aaacgtcata gcccggagag    540
cgacccgtta atgctggtat ggcggcgga tcatgtgatt gccgatgaag acgcgttccg    600
tgccgccgtg cgtaatgcca tgccatatgc cgaagcgggc aagctggtga ccttcggcat    660
tgtgccggat ctaccagaaa ccggttatgg ctatattcgt cgcggtgaag tgtctgcggg    720
tgagcaggat atggtggcct ttgaagtggc gcagtttgtc gaaaaaccga atctggaaac    780
cgctcaggcc tatgtggcaa gcggcgaata ttactggaac agcggtatgt tcctgttccg    840
cgccggacgc tatctcgaag aactgaaaaa atatcgcccg gatatcctcg atgcctgtga    900
aaaagcgatg agcgccgtcg atccggatct caatttattt cgcgtggatg aagaagcgtt    960
tctcgcctgc ccggaagagt cggtggatta cgcggtcatg gaacgtacgg cagatgctgt   1020
tgtggtgccg atggatgcgg gctggagcga tgttggctcc tggtcttcat tatgggagat   1080
cagcgcccac accgccgagg gcaacgtttg ccacggcgat gtgattaatc acaaaactga   1140
aaacagctat gtgtatgctg aatctggcct ggtcaccacc gtcggggtga agatctggt   1200 agtggtgcag accaaagatg cggtgctgat tgccgaccgt aacgcggtac aggatgtgaa   1260
aaaagtggtc gagcagatca aagccgatgg tcgccatgag catcgggtgc atcgcgaagt   1320
gtatcgtccg tggggcaaat atgactctat cgacgcgggc gaccgctacc aggtgaaacg   1380
catcaccgtg aaaccgggcg agggcttgtc ggtacagatg caccatcacc gcgcggaaca   1440
ctgggtggtt gtcgcgggaa cggcaaaagt caccattgat ggtgatatca aactgcttgg   1500
tgaaaacgag tccatttata ttccgctggg ggcgacgcat tgcctggaaa acccggggaa   1560
aattccgctc gatttaattg aagtgcgctc cggctcttat ctcgaagagg atgatgtggt   1620
gcgtttcgcg gatcgctacg gacgggtgta aacgtcgcat caggcaatga atgcgaaacc   1680
gcggtgtaaa taacgacaaa aataaaattg gccgcttcgg tcagggccaa ctattgcctg   1740
aaaaagggta acgatatgaa aaaattaacc tgctttaaag cctatgatat tcgcgggaaa   1800
ttaggcgaag aactgaatga agatatcgcc tggcgcattg gtcgcgccta tggcgaattt   1860
ctcaaaccga aaaccattgt gttaggcggt gatgtccgcc tcaccagcga aaccttaaaa   1920
ctggcgctgg cgaaaggttt acaggatgcg ggcgttgacg tgctggatat tggtatgtcc   1980
ggcaccgaag agatctatttt cgccacgttc catctcggcg tggatggcgg cattgaagtt   2040
accgccagcc ataatccgat ggattataac ggcatgaagc tggttcgcga gggggctcgc   2100
ccgatcagcg gagataccgg actgcgcgac gtccagcgtc tggctgaagc caacgacttt   2160
cctcccgtcg atgaaaccaa acgcggtcgc tatcagcaaa tcaacctgcg tgacgcttac   2220
gttgatcacc tgttcggtta tatcaatgtc aaaaacctca cgccgctcaa gctggtgatc   2280 aactcccggga acggcgcagc gggtccggtg gtggacgcca ttgaagcccg ctttaaagcc   2340
ctcgcgcgcg ccgtggaatt aatcaaagtg cacaacacgc cggacggcaa tttccccaac   2400
ggtattccta acccactact gccggaatgc cgcgacgaca cccgcaatgc ggtcatcaaa   2460
```

```
cacggcgcgg atatgggcat tgcttttgat ggcgattttg accgctgttt cctgtttgac    2520
gaaaaagggc agtttattga gggctactac attgtcggcc tgttggcaga agcattcctc    2580
gaaaaaaatc ccggcgcgaa gatcatccac gatccacgtc tctcctggaa caccgttgat    2640
gtggtgactg ccgcaggtgg cacgccggta atgtcgaaaa ccggacacgc ctttattaaa    2700
gaacgtatgc gcaaggaaga cgccatctat ggtggcgaaa tgagcgccca ccattacttc    2760
cgtgatttcg cttactgcga cagcggcatg atcccgtggc tgctggtcgc cgaactggtg    2820
tgcctgaaag ataaaacgct gggcgaactg gtacgcgacc ggatggcggc gtttccggca    2880
agcggtgaga tcaacagcaa actggcgcaa cccgttgagg cgattaaccg cgtggaacag    2940
cattttagcc gtgaggcgct ggcggtggat cgcaccgatg gcatcagcat gacctttgcc    3000
gactggcgct ttaacctgcg cacctccaat accgaaccgg tggtgcgcct gaatgtggaa    3060
tcgcgcggtg atgtgccgct gatggaagcg cgaacgcgaa ctctgctgac gttgctgaac    3120
gagtaaaaac gcggccgcga tatcgttgta aaacgacggc cagtgcaaga atcataaaaa    3180
atttatttgc tttcaggaaa atttttctgt ataatagatt cataaatttg agagaggagt    3240
ttttgtgagc ggataacaat tccccatctt agtatattag ttaagtataa ataccaccgcg    3300 gaggacgaag gagatagaac catgtcaaaa gtcgctctca tcaccggtgt aaccggacaa    3360
gacggttctt acctggcaga gtttctgctg gaaaaaggtt acgaggtgca tggtattaag    3420
cgtcgcgcat cgtcattcaa caccgagcgc gtggatcaca tttatcagga tccgcacacc    3480
tgcaacccga aattccatct gcattatggc gacctgagtg atacctctaa cctgacgcgc    3540
attttgcgtg aagtacagcc ggatgaagtg tacaacctgg gcgcaatgag ccacgttgcg    3600
gtctcttttg agtcaccaga atataccgct gacgtcgacg cgatgggtac gctgcgcctg    3660
ctggaggcga tccgcttcct cggtctggaa agaaaactc gtttctatca ggcttccacc    3720
tctgaactgt atggtctggt gcaggaaatt ccgcagaaag agaccacgcc gttctacccg    3780
cgatctccgt atgcggtcgc caaactgtac gcctactgga tcaccgttaa ctaccgtgaa    3840
tcctacggca tgtacgcctg taacggaatt ctcttcaacc atgaatcccc gcgccgcggc    3900
gaaaccttcg ttacccgcaa aatcacccgc gcaatcgcca acatcgccca ggggctggag    3960
tcgtgcctgt acctcggcaa tatggattcc ctgcgtgact ggggccacgc caaagactac    4020
gtaaaaatgc agtggatgat gctgcagcag gaacagccgg aagatttcgt tatcgcgacc    4080
ggcgttcagt actccgtgcg tcagttcgtg gaaatggcgg cagcacagct gggcatcaaa    4140
ctgcgctttg aaggcacggg cgttgaagag aagggcattg tggtttccgt caccgggcat    4200
gacgcgccgg cgttaaaccc gggtgatgtg attatcgctg ttgacccgcg ttacttccgt    4260
ccggctgaag ttgaaacgct gctcggcgac ccgaccaaag cgcacgaaaa actgggctgg    4320
aaaccggaaa tcaccctcag agagatggtg tctgaaatgg tggctaatga cctcgaagcg    4380
gcgaaaaaac actctctgct gaaatctcac ggctacgacg tggcgatcgc gctggagtca    4440
taagcatgag taaacaacga gtttttattg ctggtcatcg cgggatggtc ggttccgcca    4500
tcaggcggca gctcgaacag cgcggtgatg tggaactggt attacgcacc cgcgacgagc    4560
tgaacctgct ggacagccgc gccgtgcatg atttcttttgc cagcgaacgt attgaccagg    4620
tctatctggc ggcggcgaaa gtgggcggca ttgttgccaa caacacctat ccggcggatt    4680
tcatctacca gaacatgatg attgagagca acatcattca cgccgcgcat cagaacgacg    4740
tgaacaaact gctgttttctc ggatcgtcct gcatctaccc gaaactggca aaacagccga    4800
```

```
tggcagaaag cgagttgttg cagggcacgc tggagccgac taacgagcct tatgctattg    4860
ccaaaatcgc cgggatcaaa ctgtgcgaat catacaaccg ccagtacgga cgcgattacc    4920
gctcagtcat gccgaccaac ctgtacgggc cacacgacaa cttccacccg agtaattcgc    4980
atgtgatccc agcattgctg cgtcgcttcc acgaggcgac ggcacagaat gcgccggacg    5040
tggtggtatg gggcagcggt acaccgatgc gcgaatttct gcacgtcgat gatatggcgg    5100
cggcgagcat tcatgtcatg gagctggcgc atgaagtctg gctggagaac acccagccga    5160
tgttgtcgca cattaacgtc ggcacgggcg ttgactgcac tatccgcgag ctggcgcaaa    5220
ccatcgccaa agtggtgggt tacaaaggcc gggtggtttt tgatgccagc aaaccggatg    5280
gcacgccgcg caaactgctg gatgtgacgc gcctgcatca gcttggctgg tatcacgaaa    5340
tctcactgga agcggggctt gccagcactt accagtggtt ccttgagaat caagaccgct    5400 ttcgggggggg gagctaacgc gccatttaaa tcaacctcag cggtcatagc tgtttcctgt    5460
gactgagcaa taactagcat aaccccttgg ggcctctaaa cgggtcttga ggggtttttt    5520
gctgaaacca atttgcctgg cggcagtagc gcggtggtcc cacctgaccc catgccgaac    5580
tcagaagtga aacgccgtag cgccgatggt agtgtggggt ctccccatgc gagagtaggg    5640
aactgccagg catcaaataa aacgaaaggc tcagtcgaaa gactgggcct ttcgggatcc    5700
aggccggcct gttaacgaat taatcttccg cggcggtatc gataagcttg atatcgaatt    5760
ccgaagttcc tattctctag aaagtatagg aacttcaggt ctgaagagga gtttacgtcc    5820
agccaagcta gcttggctgc aggtcgtcga aattctaccg ggtaggggag gcgcttttcc    5880
caaggcagtc tggagcatgc gctttagcag ccccgctggg cacttggcgc tacacaagtg    5940
gcctctggcc tcgcacacat tccacatcca ccggtaggcg ccaaccggct ccgttctttg    6000
gtggcccctt cgcgccacct tctactcctc ccctagtcag gaagttcccc cccgccccgc    6060
agctcgcgtc gtgcaggacg tgacaaatgg aagtagcacg tctcactagt ctcgtgcaga    6120
tggacagcac cgctgagcaa tggaagcggg taggcctttg gggcagcggc caatagcagc    6180
tttgctcctt cgctttctgg gctcagaggc tgggaagggg tgggtccggg ggcgggctca    6240
ggggcgggct caggggcggg gcgggcgccc gaaggtcctc cggaggcccg gcattctgca    6300
cgcttcaaaa gcgcacgtct gccgcgctgt tctcctcttc ctcatctccg ggcctttcga    6360
cctgcagcct gttgacaatt aatcatcggc atagtatatc ggcatagtat aatacgacaa    6420
ggtgaggaac taaaccatgg gtcaaagtag cgatgaagcc aacgctcccg ttgcagggca    6480
gtttgcgctt cccctgagtg ccacctttgg cttaggggat cgcgtacgca agaaatctgg    6540
tgccgcttgg cagggtcaag tcgtcggttg gtattgcaca aaactcactc ctgaaggcta    6600
tgcggtcgag tccgaatccc acccaggctc agtgcaaatt tatcctgtgg ctgcacttga    6660
acgtgtggcc taatgagggg atcaattctc tagagctcgc tgatcagaag ttcctattct    6720
ctagaaagta taggaacttc gatggcgcct catccctgaa gccaataggg ataacagggt    6780
aat                                                                  6783
```

<210> SEQ ID NO 2
<211> LENGTH: 2851
<212> TYPE: DNA
<213> ORGANISM: Artificial Sequence
<220> FEATURE:
<223> OTHER INFORMATION: integration cassette

<400> SEQUENCE: 2

```
tggccagatg attaattcct aatttttgtt gacactctat cattgataga gttatttttac    60
```

```
cactccctat cagtgataga gaaaagtgaa atgaatagtt cgacaaaaat ctagaaataa    120
ttttgtttaa ctttaagaag gagatataca aatgtactat ttaaaaaaca caaacttttg    180
gatgttcggt ttattctttt tcttttactt ttttatcatg ggagcctact tcccgttttt    240
cccgatttgg ctacatgaca tcaaccatat cagcaaaagt gatacgggta ttattttgc     300 cgctatttct ctgttctcgc tattattcca accgctgttt ggtctgcttt ctgacaaact    360
cgggctgcgc aaatacctgc tgtggattat taccggcatg ttagtgatgt ttgcgccgtt    420
ctttattttt atcttcgggc cactgttaca atacaacatt ttagtaggat cgattgttgg    480
tggtatttat ctaggctttt gttttaacgc cggtgcgcca gcagtagagg catttattga    540
gaaagtcagc cgtcgcagta atttcgaatt tggtcgcgcg cggatgtttg gctgtgttgg    600
ctgggcgctg tgtgcctcga ttgtcggcat catgttcacc atcaataatc agtttgtttt    660
ctggctgggc tctggctgtg cactcatcct cgccgtttta ctcttttcg ccaaaacgga     720 tgcgccctct tctgccacgg ttgccaatgc ggtaggtgcc aaccattcgg catttagcct    780
taagctggca ctggaactgt tcagacagcc aaaaactgtgg tttttgtcac tgtatgttat   840 tggcgttttcc tgcacctacg atgtttttga ccaacagttt gctaatttct ttacttcgtt   900
ctttgctacc ggtgaacagg gtacgcgggt atttggctac gtaacgacaa tgggcgaatt    960
acttaacgcc tcgattatgt tctttgcgcc actgatcatt aatcgcatcg gtgggaaaaa   1020
cgccctgctg ctggctggca ctattatgtc tgtacgtatt attggctcat cgttcgccac   1080
ctcagcgctg gaagtggtta ttctgaaaac gctgcatatg tttgaagtac cgttcctgct   1140
ggtgggctgc tttaaatata ttaccagcca gtttgaagtg cgttttcag cgacgattta    1200 tctggtctgt ttctgcttct taagcaact ggcgatgatt tttatgtctg tactggcggg    1260
caatatgtat gaaagcatcg gtttccaggg cgcttatctg gtgctgggtc tggtggcgct   1320
gggcttcacc ttaattccg tgttcacgct tagcggcccc ggcccgcttt ccctgctgcg    1380
tcgtcaggtg aatgaagtcg ctgggagcta agcggccgcg tcgacacgca aaaaggccat   1440
ccgtcaggat ggccttctgc ttaatttgat gcctggcagt ttatggcggg cgtcctgccc   1500
gccaccctcc gggccgttgc ttcgcaacgt tcaaatccgc tcccggcgga tttgtcctac   1560
tcaggagagc gttcaccgac aaacaacaga taaaacgaaa ggcccagtct ttcgactgag   1620
cctttcgttt tatttgatgc ctggcagttc cctactctcg catggggaga ccccacacta   1680
ccatcatgta tgaatatcct ccttagttcc tattccgaag ttcctattct ctagaaagta   1740
taggaacttc ggcgcgtcct acctgtgaca cgcgtgccgc agtctcacgc ccggagcgta   1800
gcgaccgagt gagctagcta tttgtttatt tttctaaata cattcaaata tgtatccgct   1860
catgagacaa taaccctgat aaatgcttca ataatattga aaaaggaaga gtatgaggga   1920
agcggtgatc gccgaagtat cgactcaact atcagaggta gttggcgtca tcgagcgcca   1980
tctcgaaccg acgttgctgg ccgtacattt gtacggctcc gcagtggatg gcggcctgaa   2040
gccacacagt gatattgatt tgctggttac ggtgaccgta aggcttgatg aaacaacgcg   2100
gcgagctttg atcaacgacc ttttggaaac ttcggcttcc cctggagaga gcgagattct   2160
ccgcgctgta gaagtcacca ttgttgtgca cgacgacatc attccgtggc gttatccagc   2220
taagcgcgaa ctgcaatttg gagaatggca gcgcaatgac attcttgcag gtatcttcga   2280
gccagccacg atcgacattg atctggctat cttgctgaca aaagcaagag aacatagcgt   2340
tgccttggta ggtccagcgg cggaggaact ctttgatccg gttcctgaac aggatctatt   2400
```

-continued

| | |
|---|---:|
| tgaggcgcta aatgaaacct taacgctatg gaactcgccg cccgactggg ctggcgatga | 2460 |
| gcgaaatgta gtgcttacgt tgtcccgcat ttggtacagc gcagtaaccg gcaaaatcgc | 2520 |
| gccgaaggat gtcgctgccg actgggcaat ggagcgcctg ccggcccagt atcagcccgt | 2580 |
| catacttgaa gctagacagg cttatcttgg acaagaagaa gatcgcttgg cctcgcgcgc | 2640 |
| agatcagttg gaagaatttg tccactacgt gaaaggcgag atcaccaagg tagtcggcaa | 2700 |
| ataatgtcta acaattcgtt caagccgagg ggccgcaaga tccggccacg atgacccggt | 2760 |
| cgtcgggtac cggcagggcg gggcgtaagg cgcgccattt aaatgaagtt cctattccga | 2820 |
| agttcctatt ctctagaaag tataggaact t | 2851 |

<210> SEQ ID NO 3
<211> LENGTH: 2858
<212> TYPE: DNA
<213> ORGANISM: Artificial Sequence
<220> FEATURE:
<223> OTHER INFORMATION: integration cassette

<400> SEQUENCE: 3

| | |
|---|---:|
| ggccagatga ttaattccta attttttgttg acactctatc attgatagag ttattttacc | 60 |
| actccctatc agtgatagag aaaagtgaaa tgaatagttc gacaaaaatc tagaaataat | 120 |
| tttgttttaac tttaagaagg agatatacaa atgggcagca ttattcgtct gcagggtggt | 180 |
| ctgggtaatc agctgtttca gtttagcttt ggttatgccc tgagcaaaat taatggtaca | 240 |
| ccgctgtatt tcgacattag ccattatgcc gaaaacgatg atcatggtgg ttatcgtctg | 300 |
| aataatctgc agattccgga agaatatctg cagtattata ccccgaaaat taataatatt | 360 |
| tataaactgc tggtgcgtgg cagccgtctg tatccggata ttttttctgtt tctgggcttt | 420 |
| tgcaacgaat tcatgcccta tggctacgat tttgaatata ttgcccagaa atggaaaagc | 480 |
| aaaaaataca ttggctactg gcagagcgaa cacttttttc ataaacatat tctggacctg | 540 |
| aaagaatttt ttattccgaa aaatgtgagc gaacaggcaa atctgctggc agcaaaaatt | 600 |
| ctggaaagcc agagcagcct gagcattcat attcgtcgtg gcgattatat taaaaacaaa | 660 |
| accgcaaccc tgacacatgg tgtttgtagc ctggaatatt ataaaaaagc cctgaacaaa | 720 |
| atccgcgatc tggcaatgat tcgtgatgtg tttatcttta gcgacgatat cttctggtgc | 780 |
| aaagaaaata ttgaaaccct gctgagcaaa aaatataata tttattatag cgaagatctg | 840 |
| agccaagaag aggatctgtg gctgatgagc ctggcaaatc atcatattat tgccaatagc | 900 |
| agctttagtt ggtggggtgc atatctgggt agcagcgcaa gccagattgt tatttatccg | 960 |
| accccgtggt atgatattac cccgaaaaac acctatatcc gattgtgaa ccattggatc | 1020 |
| aacgttgata acatagcag ctgctaagcg gccgcgtcga cacgcaaaaa ggccatccgt | 1080 |
| caggatggcc ttctgcttaa tttgatgcct ggcagtttat ggcggcgtc ctgcccgcca | 1140 |
| ccctccgggc cgttgcttcg caacgttcaa atcgctcccc ggcggatttg tcctactcag | 1200 |
| gagagcgttc accgacaaac aacagataaa acgaaaggcc cagtctttcg actgagcctt | 1260 |
| tcgttttatt tgatgcctgg cagttcccta ctctcgcatg gggagacccc acactaccat | 1320 |
| catgtatgaa tatcctcctt agttcctatt ccgaagttcc tattctctag aaagtatagg | 1380 |
| aacttcggcg cgtcctacct gtgacacgcg tcaagatccc ctcacgctgc cgcaagcact | 1440 |
| cagggcgcaa gggctgctaa aggaagcgga acacgtagaa agccagtccg cagaaacggt | 1500 |
| gctgaccccg gatgaatgtc agctactggg ctatctggac aagggaaaac gcaagcgcaa | 1560 |
| agagaaagca ggtagcttgc agtgggctta catggcgata gctagactgg gcggttttat | 1620 |

| | |
|---|---|
| ggacagcaag cgaaccggaa ttgccagctg gggcgccctc tggtaaggtt gggaagccct | 1680 |
| gcaaagtaaa ctggatggct ttcttgccgc caaggatctg atggcgcagg ggatcaagat | 1740 |
| ctgatcaaga acaggatga ggatcgtttc gcatgattga acaagatgga ttgcacgcag | 1800 |
| gttctccggc cgcttgggtg agagggctat tcggctatga ctgggcacaa cagacaatcg | 1860 |
| gctgctctga tgccgccgtg ttccggctgt cagcgcaggg gcgcccggtt cttttttgtca | 1920 |
| agaccgacct gtccggtgcc ctgaatgaac tgcaggacga ggcagcgcgg ctatcgtggc | 1980 |
| tggccacgac gggcgttcct tgcgcagctg tgctcgacgt tgtcactgaa gcgggaaggg | 2040 |
| actggctgct attgggcgaa gtgccggggc aggatctcct gtcatctcac cttgctcctg | 2100 |
| ccgagaaagt atccatcatg gctgatgcaa tgcggcggct gcatacgctt gatccggcta | 2160 |
| cctgcccatt cgaccaccaa gcgaaacatc gcatcgagcg agcacgtact cggatggaag | 2220 |
| ccggtcttgt cgatcaggat gatctggacg aagagcatca ggggctcgcg ccagccgaac | 2280 |
| tgttcgccag gctcaaggcg cgcatgcccg acggcgagga tctcgtcgtg acccatggcg | 2340 |
| atgcctgctt gccgaatatc atggtggaaa atggccgctt ttctggattc atcgactgtg | 2400 |
| gccggctggg tgtggcggac cgctatcagg acatagcgtt ggctacccgt gatattgctg | 2460 |
| aagagcttgg cggcgaatgg gctgaccgct tcctcgtgct ttacggtatc gccgctcccg | 2520 |
| attcgcagcg catcgccttc tatcgccttc ttgacgagtt cttctgagcg ggactctggg | 2580 |
| gttcgaaatg accgaccaag cgacgcccaa cctgccatca cgagatttcg attccaccgc | 2640 |
| cgccttctat gaaaggttgg gcttcggaat cgttttccgg gacgccggct ggatgatcct | 2700 |
| ccagcgcggg gatctcatgc tggagttctt cgcccacccc agcttcaaaa gcgctctcgg | 2760 |
| taccggcagg gcggggcgta aggcgcgcca tttaaatgaa gttcctattc cgaagttcct | 2820 |
| attctctaga aagtatagga acttcgaagc agctccag | 2858 |

<210> SEQ ID NO 4
<211> LENGTH: 2631
<212> TYPE: DNA
<213> ORGANISM: Artificial Sequence
<220> FEATURE:
<223> OTHER INFORMATION: integration cassette

<400> SEQUENCE: 4

| | |
|---|---|
| ggccagatga ttaattccta attttttgttg acactctatc attgatagag ttattttacc | 60 |
| actccctatc agtgatagag aaaagtgaaa tgaatagttc gacaaaaatc tagaaataat | 120 |
| tttgttttaac tttaagaagg agatatacaa atgaagtcgg cactgacctt tcccgtcgc | 180 |
| atcaatccgg tgtttctggc gttctttgtc gttgcttttc tgagcggtat cgcaggcgca | 240 |
| ctgcaggctc cgaccctgag tctgtttctg tccacggaag tgaaagttcg tccgctgtgg | 300 |
| gttggtctgt tctataccgt caacgcaatc gctggcatta cggttagctt tatcctggcg | 360 |
| aaacgttcag attcgcgcgg tgaccgtcgc aagctgatta tggtgtgcta tctgatggcg | 420 |
| gttggcaact gtctgctgtt tgccttcaat cgtgattacc tgaccctgat cacggcaggt | 480 |
| gtgctgctgg cgagcgttgc caacaccgca atgccgcaga ttttcgcgct ggcccgtgaa | 540 |
| tatgccgaca gctctgcacg cgaagtggtt atgtttagtt ccatcatgcg cgctcaactg | 600 |
| agtctggcat gggtgattgg tccgccgctg tcctttatgc tggcgctgaa ttacggttttt | 660 |
| accctgatgt tctcaatcgc ggccggcatt ttcgttctgt cggccctggt cgtgtggttt | 720 |
| atcctgccga gtgtcccgcg tgcagaaccg gttgtcgatg caccggtggt tgtccagggt | 780 |

| | |
|---|---:|
| tcactgttcg cagacaaaaa cgttctgctg ctgtttatcg cgtcgatgct gatgtggacc | 840 |
| tgcaatacga tgtatattat cgatatgccg ctgtacatta ccgcaagcct gggtctgccg | 900 |
| gaacgtctgg ctggtctgct gatgggtacc gcagctggcc tggaaattcc gatcatgctg | 960 |
| ctggcgggtt attctgtgcg ttactttggc aaacgcaaga ttatgctgtt cgctgttctg | 1020 |
| gcgggtgtcc tgttttatac cggcctggtt ctgtttaaat tcaagacggc cctgatgctg | 1080 |
| ctgcagatct ttaacgcaat tttcatcggt attgtggctg cattggtat gctgtacttc | 1140 |
| caagatctga tgccgggtcg tgcaggtgca gcaaccacgc tgtttaccaa tagcatctct | 1200 |
| acgggtgtca ttctggcagg cgtgctgcaa ggcggtctga ccgaaacgtg gggccatgac | 1260 |
| agcgtctatg tgatggcgat ggtcctgtct attctggccc tgattatctg tgcacgtgtg | 1320 |
| cgcgaagctt aaatcgatac tagcataacc ccttggggcc tctaaacgcg tcgacacgca | 1380 |
| aaaaggccat ccgtcaggat ggccttctgc ttaatttgat gcctggcagt ttatggcggg | 1440 |
| cgtcctgccc gccaccctcc gggccgttgc ttcgcaacgt tcaaatccgc tcccggcgga | 1500 |
| tttgtcctac tcaggagagc gttcaccgac aaacaacaga taaaacgaaa ggcccagtct | 1560 |
| ttcgactgag cctttcgttt tatttgatgc ctggcagttc cctactctcg catggggaga | 1620 |
| ccccacacta ccatcatgta tgaatatcct ccttagttcc tattccgaag ttcctattct | 1680 |
| ctagaaagta taggaacttc ggcgcgtcct acctgtgacg gaagatcact tcgcagaata | 1740 |
| aataaatcct ggtgtccctg ttgataccgg gaagccctgg gccaacttttt ggcgaaaatg | 1800 |
| agacgttgat cggcacgtaa gaggttccaa cttcaccat aatgaaataa gatcactacc | 1860 |
| gggcgtattt tttgagttgt cgagattttc aggagctaag gaagctaaaa tggagaaaaa | 1920 |
| aatcactgga tataccaccg ttgatatatc ccaatggcat cgtaaagaac attttgaggc | 1980 |
| atttcagtca gttgctcaat gtacctataa ccagaccgtt cagctggata ttacggcctt | 2040 |
| tttaaagacc gtaaagaaaa ataagcacaa gttttatccg gcctttattc acattcttgc | 2100 |
| ccgcctgatg aatgctcatc cggaattacg tatggcaatg aaagacggtg agctggtgat | 2160 |
| atgggatagt gttcacccct tgttacaccgt tttccatgag caaactgaaa cgttttcatc | 2220 |
| gctctggagt gaataccacg acgatttccg gcagtttcta cacatatatt cgcaagatgt | 2280 |
| ggcgtgttac ggtgaaaacc tggcctattt ccctaaaggg tttattgaga atatgttttt | 2340 |
| cgtctcagcc aatccctggg tgagtttcac cagttttgat ttaaacgtgg ccaatatgga | 2400 |
| caacttcttc gcccccgttt tcaccatggg caaatattat acgcaaggcg acaaggtgct | 2460 |
| gatgccgctg gcgattcagg ttcatcatgc cgtttgtgat ggcttccatg tcggcagatg | 2520 |
| cttaatgaat acaacagtac tgcgatgagt ggcagggcgg ggcgtaaggc gcgccattta | 2580 |
| aatgaagttc ctattccgaa gttcctattc tctagaaagt ataggaactt c | 2631 |

<210> SEQ ID NO 5
<211> LENGTH: 4259
<212> TYPE: DNA
<213> ORGANISM: Artificial Sequence
<220> FEATURE:
<223> OTHER INFORMATION: integration cassette

<400> SEQUENCE: 5

| | |
|---|---:|
| ttactcagca ataaactgat attccgtcag gctggaatac tcttcgccag gacgcaggaa | 60 |
| gcagtccggt tgcggccatt cagggtggtt cgggctgtcc ggtagaaact cgctttccag | 120 |
| agccagccct tgccagtcgg cgtaaggttc ggttccccgc gacggtgtgc cgccgaggaa | 180 |
| gttgccggag tagaattgca gagccggagc ggtggtgtag accttcagct gcaatttttc | 240 |

```
atctgctgac cagacatgcg ccgccacttt cttgccatcg cctttggcct gtaacaagaa    300
tgcgtgatcg taacctttca ctttgcgctg atcgtcgtcg gcaagaaact cactggcgat    360
gattttggcg ctgcggaaat caaaagacgt tccggcgaca gatttcaggc cgtcgtgcgg    420
aatgccgcct tcatcaaccg gcagatattc gtccgccaga atctgcaact tgtgattgcg    480
cacgtcagac tgctcgccgt caagattgaa atagacgtga ttagtcatat tcaccgggca    540
aggtttatca actgtggcgc gataagtaat ggagatacgg ttatcgtcgg tcagacgata    600
ttgcaccgtc gcgccgagat tacccgggaa gccctgatca ccatcatctg aactcagggc    660
aaacagcacc tgacgatcgt tctggttcac aatctgccag cgacgtttgt cgaacccttc    720
cggcccgccg tgcagctggt taacgccctg acttggcgaa agcgtcacgg tttcaccgtc    780
aaaggtataa cggctattgg cgatacggtt ggcataacga ccaatagagg cccccagaaa    840
cgcggcctga tcctgatagc attccgggct ggcacagccg agcagcgcct cgcggacgct    900
gccatcggaa agcggaatac gggcggaaag taaagtcgca ccccagtcca tcagcgtgac    960
taccatccct gcgttgttac gcaaagttaa cagtcggtac ggctgaccat cgggtgccag   1020
tgcgggagtt tcgttcagca ctgtcctgct ccttgtgatg gtttacaaac gtaaaaagtc   1080
tctttaatac ctgttttgc ttcatattgt tcagcgacag cttgctgtac ggcaggcacc   1140
agctcttccg ggatcagcgc gacgatacag ccgccaaatc cgccgccggt catgcgtacg   1200
ccacctttgt cgccaatcac agctttgacg atttctacca gagtgtcaat ttgcggcacg   1260
gtgatttcga aatcatcgcg catagaggca tgagactccg ccatcaactc gcccatacgt   1320
ttcaggtcgc cttgctccag cgcgctggca gcttcaacgg tgcgggcgtt ttcagtcagt   1380
atatgacgca cgcgttttgc cacgatcggg tccagttcat gcgcaacagc gttgaactct   1440
tcaatggtga catcacgcag ggctggctgc tggaagaaac gcgcaccggt ttcgcactgt   1500
tcacgacggg tgttgtattc gctgccaacc agggtacgtt tgaagttact gttgatgatg   1560
acgacagcca cacctttggg catggaaact gctttggtcc ccagtgagcg gcaatcgatc   1620
agcaaggcat gatctttctt gccgagcgcg gaaattagct gatccatgat cccgcagtta   1680
cagcctacaa actggttttc tgcttcctga ccgttaagcg cgatttgtgc gccgtccagc   1740
ggcagatgat aaagctgctg caatacggtt ccgaccgcga cttccagtga agcggaagaa   1800
cttaacccgg caccctgcgg cacattgccg ctgatcacca tgtccacgcc gccgaagctg   1860
ttgttacgca gttgcagatg tttcaccacg ccacgaacgt agttagccca ttgatagttt   1920
tcatgtgcga caatgggcgc atcgagggaa aactcgtcga gctgattttc ataatcggct   1980
gccatcacgc gaactttacg gtcatcgcgt ggtgcacaac tgatcacggt ttgataatca   2040
atcgcgcagg gcagaacgaa accgtcgttg tagtcggtgt gttcaccaat caaattcacg   2100
cggccaggcg cctgaatggt gtgagtggca gggtagccaa atgcgttggc aaacagagat   2160 tgtgttttt ctttcagact catttcttac actccggatt cgcgaaaatg gatatcgctg   2220
actgcgcgca aacgctctgc tgcctgttct gcggtcaggt ctcgctgggt ctctgccagc   2280
atttcataac caaccataaa tttacgtacg gtggcggagc gcagcagagg cggataaaag   2340
tgcgcgtgca gctgccagtg ttgattctct tcgccattaa atggcgcgcc gtgccagccc   2400
atagagtagg ggaaggagca ctggaagagg ttgtcataac gactggtcag cttttttcaac   2460 gccagcgcca gatcgctgcg ctgggcgtcg gtcaaatcgg tgatccgtaa aacgtgggct   2520
ttgggcagca gtagcgtttc gaacggccag gcagcccagt aaggcacgac ggctaaccag   2580
```

```
tgttcggttt cgacaacggt acggctaccg tctgccagct cgcgctgaac ataatccacc    2640
agcattggtg atttctgttc ggcaaaatat tcttttttgca ggcggtcttc gcgctcagct    2700
tcgttaggca ggaagctatt tgcccaaatc tgaccgtgcg gatgcgggtt agagcagccc    2760
atcgccgcgc ctttgttttc aaaaacctgc acccatgggt acgttttccc cagttctgcg    2820
gtttgctcct gccaggtttt gacgatttcc gtcaatgctg caacgctgag ctctggcagc    2880
gttttactgt gatccggtga aaagcagatc acccggctgg tgccgcgcgc gctctggcaa    2940
cgcatcagcg gatcgtgact ttctggcgca tctggcgtgt cagacatcaa agccgcaaag    3000
tcattagtga aaacgtaagt cccggtgtaa tcggggtttt tatcgcctgt cacccgcaca    3060
ttacctgcgc agaggaagca atctggatcg tgcgcaggta acacctgttt ggctggcgtt    3120
tcctgcgccc cctgccaggg gcgcttagcg cggtgcggtg aaaccagaat ccattgcccg    3180
gtgagcgggt tgtagcggcg atgtggatga tcaacgggat taaattgcgt catggtcgtt    3240
ccttaatcgg gatatccctg tggatggcgt gactgccagt gccaggtgtc ctgcgccatt    3300
tcatcgagtg tgcgcgttac gcgccagttc agttcacggt cggctttgct ggcgtccgcc    3360
cagtaggccg aaggtcgcc ctcgcgacgc ggtgcaaaat gataattaac cggtttgccg    3420
caggctttgc tgaaggcatt aaccacgtcc agcacgctgt tgcctacgcc agcgccgagg    3480
ttgtagatgt gtacgcctgg cttgttcgcc agttttttcca tcgccacgac gtgaccgtcc    3540
gccagatcca ttacgtggat gtaatcgcgt acgccagtac catcttcggt cggataatcg    3600
ttaccaaaaa tcgccagcga gtcgcgacgg cctacagcaa cctgggcgat gtatggcatc    3660
aggttattcg gaatgccttg cggatcttcg cccatatcgc ccgacggatg cgcgccaacc    3720
gggttgaagt agcgcagcag ggcaatgctc cagtccggct gggcttttg cagatcggtg    3780 aggatctgtt ccaccatcag cttgcttttg ccgtaagggc tttgcggtgt gccggtcggg    3840
aagctttcaa cgtatggaat tttgggctga tcgccataaa cggtggcgga ggagctaaaa    3900
ataaagtttt tgacgttagc ggcgcgcatg gcgctaatca ggcgcagagt gccgttgaca    3960
ttgttgtcgt aatattccag cggttttttgt accgattcgc ccacggcttt cagcccggcg    4020
aagtggatca cggtgtcgat agcgtgatcg tgcaggatct cggtcatcaa cgcttcgtta    4080
cgaatatcgc cttcaacaaa cgttggatgt ttgccgccta aacgctcgat aacaggcagt    4140
acgctgcgct tactgttaca gaggttatca agaatgatga catcatgacc gttttgcagt    4200
aattgcacac aggtatgact tccaatgtaa ccgctaccac cggtaaccag aactctcat    4259

<210> SEQ ID NO 6
<211> LENGTH: 4223
<212> TYPE: DNA
<213> ORGANISM: Artificial Sequence
<220> FEATURE:
<223> OTHER INFORMATION: integration cassette

<400> SEQUENCE: 6
tggccagatg attaattcct aatttttgtt gacactctat cattgataga gttatttttac     60 cactccctat cagtgataga gaaaagtgaa atgaatagtt cgacaaaaat ctagaaataa    120
ttttgtttaa cttaagaag gagatataca atgcaaaaa ctactatctt taccgtccaa    180
tctggttcag tcttttcatg aactggagag ggtgaatcgt accgattggt tttgtacttc    240
cgacccggta ggtaagaaac ttggttccgg tggtggaaca tcctggctgc ttgaagaatg    300
ttataatgaa tattcagatg gtgctacttt tggagagtgg cttgaaaaag aaaaagaat    360 tcttcttcat gcgggtgggc aaagccgtcg tttacccggc tatgcacctt ctggaaagat    420
```

```
tctcactccg gttcctgtgt tccggtggga gagagggcaa catctgggac aaaatctgct      480
ttctctgcaa cttcccctat atgaaaaaat catgtctttg gctccggata aactccatac      540
actgattgcg agtggtgatg tctatattcg ttcggagaaa cctttgcaga gtattcccga      600
agcggatgtg gtttgttatg gactgtgggt agatccgtct ctggctaccc atcatggcgt      660
gtttgcttcc gatcgcaaac atcccgaaca actcgacttt atgcttcaga agccttcgtt      720
ggcagaattg gaatctttat cgaagaccca tttgttcctg atggacatcg gtatatggct      780
tttgagtgac cgtgccgtag aaatcttgat gaaacgttct cataaagaaa gctctgaaga      840
actaaagtat tatgatcttt attccgattt tggattagct ttgggaactc atccccgtat      900
tgaagacgaa gaggtcaata cgctatccgt tgctattctg cctttgccgg aggagagtt       960 ctatcattac gggaccagta aagaactgat tcttcaact ctttccgtac agaataaggt      1020
ttacgatcag cgtcgtatca tgcaccgtaa agtaaagccc aatccggcta tgtttgtcca     1080
aaatgctgtc gtgcggatac ctcttttgtgc cgagaatgct gatttatgga tcgagaacag    1140
tcatatcgga ccaaagtgga agattgcttc acgacatatt attaccgggg ttccggaaaa     1200
tgactggtca ttggctgtgc ctgccggagt gtgtgtagat gtggttccga tgggtgataa     1260
gggctttgtt gcccgtccat acggtctgga cgatgttttc aaaggagatt tgagagattc     1320
caaaacaacc ctgacgggta ttccttttgg tgaatggatg tccaaacgcg gtttgtcata    1380
tacagatttg aaaggacgta cggacgattt acaggcagtt tccgtattcc ctatggttaa     1440
ttctgtagaa gagttgggat tggtgttgag gtggatgttg tccgaacccg aactggagga     1500
aggaaagaat atctggttac gttccgaaca ttttttctgcg gacgaaattt cggcaggtgc    1560
caatctgaag cgtttgtatg cacaacgtga agagttcaga aaaggaaact ggaaagcatt    1620
ggccgttaat catgaaaaaa gtgttttta tcaacttgat ttggccgatg cagctgaaga    1680
ttttgtacgt cttggtttgg atatgcctga attattgcct gaggatgctc tgcagatgtc     1740
acgcatccat aaccggatgt tgcgtgcgcg tattttgaaa ttagacggga agattatcg     1800 tccggaagaa caggctgctt ttgatttgct tcgtgacggc ttgctggacg ggatcagtaa    1860
tcgtaagagt accccaaaat tggatgtata ttccgatcag attgtttggg gacgtagccc    1920
cgtgcgcatc gatatggcag gtggatggac cgatactcct ccttattcac tttattcggg     1980
aggaaatgtg gtgaatctag ccattgagtt gaacggacaa cctcccttac aggtctatgt    2040
gaagccgtgt aaagacttcc atatcgtcct gcgttctatc gatatgggtg ctatggaaat     2100
agtatctacg tttgatgaat tgcaagatta taagaagatc ggttcacctt tctctattcc    2160
gaaagccgct ctgtcattgg caggctttgc acctgcgttt tctgctgtat cttatgcttc     2220
attagaggaa cagcttaaag atttcggtgc aggtattgaa gtgactttat ggctgctat     2280 tcctgccggt tccggtttgg gcaccagttc cattctggct tctaccgtac ttggtgccat    2340
taacgatttc tgtggtttag cctgggataa aaatgagatt tgtcaacgta ctcttgttct    2400
tgaacaattg ctgactaccg gaggtggatg gcaggatcag tatggaggtg tgttgcaggg    2460
tgtgaagctt cttcagaccg aggccggctt tgctcaaagt ccattggtgc gttggctacc    2520
cgatcattta tttacgcatc ctgaatacaa agactgtcac ttgctttatt ataccggtat     2580
aactcgtacg gcaaaaggga tcttggcaga aatagtcagt tccatgttcc tcaattcatc    2640
gttgcatctc aatttacttt cggaaatgaa ggcgcatgca ttggatatga atgaagctat     2700
acagcgtgga agttttgttg agtttggccg tttggtagga aaaacctggg aacaaaacaa    2760
```

| | |
|---|---|
| agcattggat agcggaacaa atcctccggc tgtggaggca attatcgatc tgataaaaga | 2820 |
| ttataccttg ggatataaat tgccgggagc cggtggtggc gggtacttat atatggtagc | 2880 |
| gaaagatccg caagctgctg ttcgtattcg taagatactg acagaaaacg ctccgaatcc | 2940 |
| gcgggcacgt tttgtcgaaa tgacgttatc tgataaggga ttccaagtat cacgatcata | 3000 |
| actgaaacca atttgcctgg cggcagtagc gcggtggtcc cacctgaccc catgccgaac | 3060 |
| tcagaagtga aacgccgtag cgccgatggt agtgtgggt ctccccatgc gagagtaggg | 3120 |
| aactgccagg catcaaataa aacgaaaggc tcagtcgaaa gactgggcct ttcgggatcc | 3180 |
| aggccggcct gttaagacgg ccagtgaatt cgagctcggt acctaccgtt cgtataatgt | 3240 |
| atgctatacg aagttatcga gctctagaga atgatcccct cattaggcca cacgttcaag | 3300 |
| tgcagcgcac accgtggaaa cggatgaagg cacgaaccca gttgacataa gcctgttcgg | 3360 |
| ttcgtaaact gtaatgcaag tagcgtatgc gctcacgcaa ctggtccaga accttgaccg | 3420 |
| aacgcagcgg tggtaacggc gcagtggcgg ttttcatggc ttgttatgac tgtttttttg | 3480 |
| tacagtctat gcctcgggca tccaagcagc aagcgcgtta cgccgtgggt cgatgtttga | 3540 |
| tgttatggag cagcaacgat gttacgcagc agcaacgatg ttacgcagca gggcagtcgc | 3600 |
| cctaaaacaa agttaggtgg ctcaagtatg gcatcattc gcacatgtag gctcggccct | 3660 |
| gaccaagtca aatccatgcg ggctgctctt gatcttttcg gtcgtgagtt cggagacgta | 3720 |
| gccacctact cccaacatca gccggactcc gattacctcg gaacttgct ccgtagtaag | 3780 |
| acattcatcg cgcttgctgc cttcgaccaa gaagcggttg ttggcgctct cgcggcttac | 3840 |
| gttctgccca ggtttgagca gccgcgtagt gagatctata tctatgatct cgcagtctcc | 3900 |
| ggcgagcacc ggaggcaggg cattgccacc gcgctcatca atctcctcaa gcatgaggcc | 3960 |
| aacgcgcttg gtgcttatgt gatctacgtg caagcagatt acggtgacga tcccgcagtg | 4020 |
| gctctctata caaagttggg catacgggaa gaagtgatgc actttgatat cgacccaagt | 4080 |
| accgccacct aacaattcgt tcaagccgag atcgtagaat ttcgacgacc tgcagccaag | 4140 |
| cataacttcg tataatgtat gctatacgaa cggtaggatc ctctagagtc gacctgcagg | 4200 |
| catgagatgt gtataagaga cag | 4223 |

<210> SEQ ID NO 7
<211> LENGTH: 3792
<212> TYPE: DNA
<213> ORGANISM: Artificial Sequence
<220> FEATURE:
<223> OTHER INFORMATION: integration cassette

<400> SEQUENCE: 7

| | |
|---|---|
| gggaattgat tctggtacca aatgagtcga ccggccagat gattaattcc taattttgt | 60 |
| tgacactcta tcattgatag agttatttta ccactcccta tcagtgatag agaaaagtga | 120 |
| aatgaatagt tcgacaaaaa tctagaaata atttttgttta actttaagaa ggagatatac | 180 |
| aaatgattac ccgcaaaagg cgggccagga caatccatag ccgatatcca atcggaattt | 240 |
| acgggagcat agtaatgaca gatattgcac agttgcttgg caaagacgcc gacaaccttt | 300 |
| tacagcaccg ttgtatgact attccttctg accagcttta tctccccgga catgactacg | 360 |
| tagaccgcgt gatgattgac aataatcgcc cgccagcggt gttacgtaat atgcagacgt | 420 |
| tgtacaacac tgggcgtctg gctggcacag gatatctttc tattctgccg gttgaccagg | 480 |
| gcgttgagca ctctgccgga gcttcatttg ctgctaaccc gctctacttt gacccgaaaa | 540 |
| acattgttga actggcgatc gaagcgggct gtaactgtgt ggcatcaact tacggcgtgt | 600 |

```
tggcgtcggt atcgcggcgc tatgcgcatc gcattccatt cctcgtcaaa cttaatcaca    660
acgagacgct aagttacccg aacacctacg atcaaacgct gtatgccagc gtggagcagg    720
ccttcaacat gggcgcggtg gcggttggtg cgactatcta ttttggttcg aagagtcac     780
gtcgccagat tgaagaaatt tctgcggctt ttgaacgtgc gcacgagctg ggcatggtga    840
cagtgctgtg ggcctatttg cgtaactccg ccttttaagaa agatggcgtt gattaccatg   900
tttccgccga cctgaccggt caggcaaacc atctggcggc gaccataggt gcagatatcg    960
tcaaacaaaa aatggcggaa aataacggcg gctataaagc aattaattac ggttataccg   1020
acgatcgcgt gtacagcaag ttaaccagcg aaaacccgat tgatctggtg cgttatcagt   1080
tagctaactg ctatatgggc cgggccgggt tgataaactc cggcggtgct gcaggcggtg   1140
aaactgacct cagcgatgca gtgcgtactg cggttatcaa caaacgcgct ggcggaatgg   1200
ggctgattct tggacgtaag gcgttcaaga atcgatggc tgacggcgtg aaactgatta    1260
acgccgtgca ggatgtttat ctcgatagca aaattactat cgcctaagag gatcgagatc   1320
tcgatcccgc gaaattaata cgactcacta taggggaatt gtgagcggat aacaattccc   1380
ctctagaaat aattttgttt aactttaaga aggagatata ccatgggcca tcatcatcat   1440
catcatcatc atcatcacag cagcggccat atcgaaggtc gtcatatggc ggtgaaagaa   1500
gcgaccagcg agaccaagaa gcgtagcggt tacgagatca ttaccctgac cagctggctg   1560
ctgcaacaag aacagaaggg tatcattgac gcggaactga ccatcgttct gagcagcatt   1620
agcatggcgt gcaaacagat cgcgagcctg gtgcaacgtg cgaacattag caacctgacc   1680
ggtacccaag gcgcggttaa catccagggt gaagaccaaa agaaactgga tgttattagc   1740
aacgaggtgt tcagcaactg cctgcgtagc agcggtcgta ccggcatcat tgcgagcgag   1800
gaagaggacg tggcggttgc ggtggaagag agctacagcg gtaactatat cgtggttttt   1860
gacccgctgg atggcagcag caacctggat gcggctgtga gcaccggtag catcttcggc   1920
atttacagcc cgaacgacga gagcctgccg gattttggtg acgatagcga cgataacacc   1980
ctgggcaccg aagagcaacg ttgcatcgtt aacgtgtgcc aaccgggtag caacctgctg   2040
gcggcgggct actgcatgta tagcagcagc gttgcgttcg tgctgaccat ggcaagggc    2100
gttttcgtgt ttaccctgga cccgctgtac ggtgaattcg tgctgaccca ggagaacctg   2160
caaatcccga gagcggtga atttacagc tttaacgagg gcaactataa actgtgggat     2220
gaaaacctga gaaatatat cgacgatctg aaggaaccgg gtccgagcgg taaaccgtac    2280
agcgcgcgtt atatcggtag cctggttggc gacttccacc gtaccctgct gtacggtggc   2340
atttacggtt atccgcgtga taagaaaagc aagaacggca aactgcgtct gctgtatgaa   2400
tgcgcgccga tgagctttat tgttgagcag gcgggtggca aggtagcga cggccaccag   2460
cgtgtgctgg atatccaacc gaccgaaatt caccagcgtg ttccgctgta cattggtagc   2520
accgaagagg ttgaaaaagt tgaaaagtat ctggcgtaat cgagtctggt aaagaaaccg   2580
ctgctgcgaa atttgaacgc cagcacatgg actcgtctac tagcgcagct taattaacct   2640
aggctgctgc caccgctgag caataactag cataacccct tggggcctct aaacgggtct   2700
tgaggggttt tttgctgaaa ggaggaacta tatccggatt ggcgaatggg acgcgccctg   2760
tagcggcgca ttaagcgcgg cgggtggacg gccagtgaat tcgagctcgg tacctaccgt   2820
tcgtataatg tatgctatac gaagttatcg agctctagag aatgatcccc tcattaggcc   2880
acacgttcaa gtgcagcgca caccgtggaa acggatgaag gcacgaaccc agttgacata   2940
```

```
agcctgttcg gttcgtaaac tgtaatgcaa gtagcgtatg cgctcacgca actggtccag    3000
aaccttgacc gaacgcagcg gtggtaacgg cgcagtggcg gttttcatgg cttgttatga    3060 ctgtttttt gtacagtcta tgcctcgggc atccaagcag caagcgcgtt acgccgtggg    3120
tcgatgtttg atgttatgga gcagcaacga tgttacgcag cagcaacgat gttacgcagc    3180
agggcagtcg ccctaaaaca aagttaggtg gctcaagtat gggcatcatt cgcacatgta    3240
ggctcggccc tgaccaagtc aaatccatgc gggctgctct tgatcttttc ggtcgtgagt    3300
tcggagacgt agccacctac tcccaacatc agccggactc cgattacctc gggaacttgc    3360
tccgtagtaa gacattcatc gcgcttgctg ccttcgacca agaagcggtt gttggcgctc    3420
tcgcggctta cgttctgccc aggtttgagc agccgcgtag tgagatctat atctatgatc    3480
tcgcagtctc cggcgagcac cggaggcagg gcattgccac cgcgctcatc aatctcctca    3540
agcatgaggc caacgcgctt ggtgcttatg tgatctacgt gcaagcagat tacggtgacg    3600
atcccgcagt ggctctctat acaaagttgg gcatacggga agaagtgatg cactttgata    3660
tcgacccaag taccgccacc taacaattcg ttcaagccga gatcgtagaa tttcgacgac    3720
ctgcagccaa gcataacttc gtataatgta tgctatacga acggtaggat cctctagagt    3780
cgacctgcag gc                                                         3792

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ctgtctctta tacacatct                                                    19
```